US009545772B2

(12) United States Patent
Gracias et al.

(10) Patent No.: US 9,545,772 B2
(45) Date of Patent: Jan. 17, 2017

(54) ARRAY STRUCTURES OF CONTAINERS

(75) Inventors: David H. Gracias, Baltimore, MD (US); Yevgeniy Vladimirovich Kalinin, Baltimore, MD (US); Christina Lee Randall, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 13/806,042

(22) PCT Filed: Jun. 24, 2011

(86) PCT No.: PCT/US2011/041877
§ 371 (c)(1),
(2), (4) Date: Dec. 20, 2012

(87) PCT Pub. No.: WO2011/163618
PCT Pub. Date: Dec. 29, 2011

(65) Prior Publication Data
US 2013/0095258 A1   Apr. 18, 2013

Related U.S. Application Data

(60) Provisional application No. 61/358,069, filed on Jun. 24, 2010.

(51) Int. Cl.
*B01L 3/00* (2006.01)
*B32B 3/26* (2006.01)
*B81B 7/00* (2006.01)
*C12M 1/32* (2006.01)
(Continued)

(52) U.S. Cl.
CPC . *B32B 3/26* (2013.01); *A61F 2/04* (2013.01); *B01L 3/50255* (2013.01); *B81B 7/0003* (2013.01); *C12M 23/12* (2013.01); *C12M 29/04* (2013.01); *B01L 2200/12* (2013.01); *B01L 2300/0819* (2013.01); *B01L 2300/0893* (2013.01); *Y10T 428/249971* (2015.04); *Y10T 428/249997* (2015.04); *Y10T 428/268* (2015.01)

(58) Field of Classification Search
CPC .............. B01L 5/5025; B01L 5/5088; B01L 2300/0819; B01L 2300/089; B01L 3/5025; B01L 3/50255; B01L 3/5085; B01L 2300/0829; B01L 2300/0896
USPC ............. 422/68.1, 502, 503, 504, 506, 507, 547,422/551, 552
See application file for complete search history.

(56) References Cited

U.S. PATENT DOCUMENTS

| 6,171,780 B1 * | 1/2001 | Pham et al. ............... 435/4 |
| 6,315,957 B1 * | 11/2001 | Feygin .......... B01L 3/50255 422/534 |
| 2007/0020310 A1 | 1/2007 | Gracias et al. |

(Continued)

OTHER PUBLICATIONS

P. Devos, B. De Haan, J. Pater and R. Van Schilfgaarde, Transplantation, 1996, 62, 893-899.

(Continued)

*Primary Examiner* — Jill Warden
*Assistant Examiner* — Dwayne K Handy
(74) *Attorney, Agent, or Firm* — Venable LLP; Henry J. Daley; F. Brock Riggs

(57) ABSTRACT

An array structure includes a plurality of containers arranged in a predetermined pattern. Each container of the plurality of containers has a maximum outer dimension that is less than about 1 cm, and each container of the plurality of containers has a substantially predetermined porosity.

21 Claims, 19 Drawing Sheets

(51) Int. Cl.
*C12M 1/00* (2006.01)
*A61F 2/04* (2013.01)

(56) References Cited

U.S. PATENT DOCUMENTS

2008/0218299 A1   9/2008   Arnold
2009/0311190 A1   12/2009  Gracias et al.

OTHER PUBLICATIONS

T. G. Leong, A Zarafshar and D. H. Gracias, Small, 2010, 6, 792-806.
C. L. Randall, T. G. Leong, N. Bassik and D. H. Gracias, Adv. Drug Delivery Rev., 2007, 59, 1547-1561.
C. L. Randall, A Gillespie, S. Singh, T. G. Leong and D. H. Gracias, Anal. Bioanal. Chem., 2009, 393, 1217-1224.
A. Azam, K. Laflin, M. Jamal, R. Fernandes and D.H. Gracias, Biomed. Microdevices, 2010, DOI:10.1007/s10544-010-9470-x.
B. Merchant, Biologicals, 1998, 26, 49-59.
J. C. Love, L.A. Estroff, J. K. Kriebel, R. G. Nuzzo and G. M. Whitesides, Chem. Rev., 2005, 105, 1103-1170.
Charnley, M., Textor, M., Khademhosseini, A. & Lutolf, M. P, Integration Column: Microwell Arrays for Mammalian Cell Culture. Meg. Biol. 1, 625-634 (2009).
Ma, B., Zhang, G., Qin, J. & Lin, B. Characterization of Drug Metabolites and Cytotoxicity Assay Simultaneously Using an Integrated Microfluidic Device. Lab Chip. 9,232-239 (2009).
Holmes, D. & Gawad, S. The Application of Microfluidics in Biology. Meth. Mol. Bio. 583, 55-80 (2010).
Kim, L., Toh, Y. C, Voldman, J. & Yu, H. A Practical Guide to Microfluidic Perfusion Culture of Adherent Mammalian Cells. Lab Chip. 7, 681-694 (2007).
Dutta, R. C. & Dutta, A. K. Cell-interactive 3D-scaffold; Advances and. Applications. Biotech. Adv. 27, 334-339 (2009).
Rappaport, C. Review—Progress in Concept and Practice of Growing Anchorage-Dependent Mammalian Cells in Three Dimensions. In Vztro Cell Dev. Biol. 39, 187-192 (2003).
Metzen, E. M., Wolff, J., Fandrey, J. & Jelkrnan, J. Pericellular pO2 and O2 Consumption in Monolayers. Respir. Phsyiol. 100,101-110 (1991).
Malda, J., Klein, T. J. & Upton, Z. The Role of Hypoxia in the In Vitro Engineering of Tissues. Tissue Eng. 13, 2153-2162 (2007).
A. Groisman, et al., Nat. Methods 2:685-689 (2005).
A. P. Wong, et al., Biomaterials 29:1853-1861 (2008).
Y. Du, et al, Proc. Nat. Acad. Sci. USA 105:9522-9527 (2008).
T. A. Desai, et al., Biotechnol. Bioeng. 57:118-120 (1998).
J. Kwon, et al., J. Vac. Sci. Technol., B, 27:2795-2800 (2009).
S. L. Tao, et al., Nat. Protocols 1:3153-3158 (2007).
J. L. Dulong and C. Legallais, Biotechnol. Bioeng., 2007, 96, 990-998.
P. Buchwald, Theor. Biol. Med. Modell., 2009, 6, 5.
B.Gimi, et al., Biomed. Microdev. 2005, 7, 341-345 (2005).
H. Ye, et al, Angew. Chem. 46:4991-4994 (2007).

B. Gimi, et al., Cell Trans. 16:403-408 (2007).
S. Prakash, H. Soe-Lin, Trends Biomat. Artif. Organs, 18:24-35 (2004).
P. J. Hung, et al., Lab Chip 5: 44-48 (2005).
D. K. Armani, C. Liu, J. Micromech. Microeng. 10:80-84 (2000).
A. G. A Coombes, et al., Biomaterials 25:315-325 (2004).
B. W. Tillman, et al., Biomaterials 30:583-588 (2009).
A. J. Postgate, et al., Dig. Dis, Sci. 53:2732-2738 (2008).
J. Tien, et al., J. Am. Chem. Soc. 120:12670-12671 (1998).
Z. Y. Gu, et al., Langmuir 20:11308-11311 (2004).
A. Anum, et al, Biomed Microdevices (2011) 13:51-58.
A. Fritze, et al., Biochim. Biophys. Acta—Biomembranes 1758:1633-1640 (2006).
T. G. Leong, et al., Lab Chip 8:1621-1625 (2008).
C. J. Ingham, et al., Proc. Natl. Acad. Sci, USA, 104:18217-18222 (2007).
D. B. Weibel, Proc. Natl. Acad. Sci. USA, 105:18075-18076 (2008).
G. E. Wnek, G. L. Bowlin, Encyclopedia of Biomaterials and Bioengineering, Informa Healthcare, London, LTK, 2nd ed., 2008, vol. 1, pp. 8-31.
C. X. F. Lam, et al., Biomed. Mater., 3:034108-22 (2008).
J. Pena, et al., J Biomed. Mater. Res. 76A:788-797 (2006).
Y. Wan, et al., Polym. Degrad. Stab. 93:1736-1741 (2008).
C. Randall, et al, Lab Chip, 2011, 11, 127.
S. Rhee, Exp. Mol. Med., 2009, 41, 858-865.
D. R. Albrecht, G. H. Underhill, T. B. Wassemlann, R. L. Sah and S. N. Bhatia, Nat. Methods, 2006, 3, 369-375.
K. Bott, Z. Upton, K. Schrobback, M. Ehrbar, J. A. Hubbell, M. P. Lutolf and S. C. Rizzi, Biomaterials, 2010, 31, 8454-8464.
K. W. Lee, S. Wang, M. J. Yaszemski and L. Lu, Biomacromolecules, 2010, 11, 682-689.
D. Gallegro-Perez, N. Higuita-Castro, S. Sharma, R. K. Reen, A. F. Palmer, K. J. Gooch, L. J. Lee, J. J. Lannutti and D. J. Hansford, Lab Chip, 2010, 10, 775-782.
A. Khademhosseini, R. Langer, J. Borenstein and J. P. Vacanti, Proc. Natl. Acad. Sci. U. S. A., 2006, 103, 2480-2487.
N. W. Choi, M. Cabodi, B. Held, J. P. Gleghorn, L. J. Bonassar and A. D. Stroock, Nat. Mater., 2007, 8, 908-915.
L. M. Bellan, S. P. Singh, P. W. Henderson, T. J. Porri, H. G. Craighead and J. A. Spector, Soft Matter, 2009, 5, 1354-1357.
B. H. Weigl, R. L. Bardell and C. R. Cabrera, Adv. Drug Delivery Rev., 2003, 55, 349-377.
P. J. Hung, P. J. Lee, P. Sabounchi, R. Lin and L. P. Lee, Biotechnol. Bioeng., 2005, 89, 1-8.
E. S. Avgoustiniatos and C. K. Colton, in Bioartificial Organs Science, Medicine, and Technology, ed. A. Prokop, D. Hunkeler and A. D. Cherrington, New York Acad Sciences, New York, 1997, pp. 145-167.
R. H. Thomlinson and L. H. Gray, Br. J. Cancer, 1955, 9, 539-549.
International Search Report and written opinion issued in PCT/US2011/041877 dated Feb. 23, 2012.
Bassik et al. "Microassembly Based on hands free Origami with Bidirection Curvature." *Applied Physics Letters* 95. (2009).
Kizilel et al. "The Bioartificial Pancreas: Progress and Challenges." *Diabetes Technologies and Therapeutics.* vol. 7, No. 6 (2005).

\* cited by examiner

ARRAY STRUCTURES OF CONTAINERS

This is a national stage application under 35 U.S.C. §371 of PCT/US2011/041877 filed Jun. 24, 2011, the entire contents of which are incorporated herein by reference and that claims priority to U.S. Provisional Application No. 61/358,069 filed Jun. 24, 2010, the entire contents of which are hereby incorporated by reference.

This invention was made with Government support of Grant No. 1-DP2-0D004346-01 awarded by the Department of Health and Human Services, The National Institutes of Health. The U.S. Government has certain rights in this invention.

BACKGROUND

1. Field of Invention

The field of the currently claimed embodiments of this invention relates to array structures, and more particularly to array structures of containers that have predetermined porosity.

2. Discussion of Related Art

It is a well-established practice in drug discovery, microbiology, tissue engineering and biotechnology to culture cells within microwell arrays (Charnley, M., Textor, M., Khademhosseini, A. & Lutolf, M. P. Integration Column: Microwell Arrays for Mammalian Cell Culture. *Meg. Biol.* 1, 625-634 (2009); Ma, B., Zhang, G., Qin, J. & Lin, B. Characterization of Drug Metabolites and Cytotoxicity Assay Simultaneously Using an Integrated Microfluidic Device. *Lab Chip.* 9, 232-239 (2009); Holmes, D. & Gawad, S. The Application of Microfluidics in Biology. *Meth. Mol. Bio.* 583, 55-80 (2010); Kim, L., Toh, Y. C, Voldman, J. & Yu, H. A Practical Guide to Microfluidic Perfusion Culture of Adherent Mammalian Cells. *Lab Chip.* 7, 681-694 (2007)). However, conventional microwell arrays do not accurately mimic the in situ cellular microenvironment due to a lack of three-dimensional (3D) cues from the external media thus generating physiologically compromised cells (Dutta, R. C. & Dutta, A. K. Cell-interactive 3D-scaffold; Advances and Applications. *Biotech. Adv.* 27, 334-339 (2009)). For example, due to limited access to the surrounding medium from only one opening (a single 2D interface) in traditional microwell arrays, hypoxic conditions resulting in decreased cell or tissue function have been reported (Rappaport, C. Review—Progress in Concept and Practice of Growing Anchorage-Dependent Mammalian Cells in Three Dimensions. In Vitro *Cell Dev. Biol.* 39, 187-192 (2003); Metzen, E. M., Wolff, J., Fandrey, J. & Jelkman, J. Pericellular $pO_2$ and $O_2$ Consumption in Monolayers. *Respir. Phsyiol.* 100, 101-110 (1991); Malda, J., Klein, T. J. & Upton, Z. The Role of Hypoxia in the In Vitro Engineering of Tissues. *Tissue Eng.* 13, 2153-2162 (2007)).

In numerous lab-on-a-chip applications where a small device size is desirable while retaining high perfusion with the surrounding medium, there is a need to transition to the third dimension. For example, to increase diffusion of media in cell culture devices, researchers have developed microfabricated chemostats with porous side walls, see A. Groisman, et al., *Nat. Methods* 2:685-689 (2005), partitioned microfluidic channels, see A. P. Wong, et al., *Biomaterials* 29:1853-1861 (2008), and microgel-based building blocks. See Y. Du, et al., *Proc. Nat. Acad. Sci. USA* 105:9522-9527 (2008). As compared to gel-based systems where porosity is a consequence of crosslinking and can have considerable spatial variability, lithographic patterning of pores offers the possibility for high precision and reproducibility. See T. A. Desai, et al., *Biotechnol. Bioeng.* 57:118-120 (1998). Although lithographic approaches have been successfully applied to microfabricated containers, in most cases, however, they feature porosity in inherently two-dimensional (2D) geometries, which allow diffusion only from the top and bottom faces. See J. Kwon, et al., *J. Vac. Sci. Technol., B,* 27:2795-2800 (2009); S. L. Tao, et al., *Nat. Protocols* 1:3153-3158 (2007). There thus remains a need for improved sub-centimeter array structures that have selectable porosities.

SUMMARY

An array structure according to an embodiment of the current invention includes a plurality of containers arranged in a predetermined pattern. Each container of the plurality of containers has a maximum outer dimension that is less than about 1 cm, and each container of the plurality of containers has a substantially predetermined porosity.

A bio-artificial pancreas according to an embodiment of the current invention includes a substrate and a plurality of porous containers attached to the substrate. The plurality of porous containers are constructed to have a size, shape and porosity such that the plurality of porous containers are suitable to contain pancreatic islet cells therein, allow insulin produced by the pancreatic islet cells to pass therethrough, and provide immuno-isolation for the pancreatic islet cells.

A dynamic display device according to an embodiment of the current invention includes a substrate and a plurality of containers attached to the substrate in a predetermined pattern. Each container has a size, shape and porosity to allow a liquid to diffuse therefrom with a predetermined diffusion pattern as a function of time when the plurality of containers are immersed in a diffusion medium while in use.

BRIEF DESCRIPTION OF THE DRAWINGS

Further objectives and advantages of the current invention will become apparent from a consideration of the description, drawings, and examples.

In FIG. 1a: (i) a clean silicon wafer is spin-coated with a sacrificial layer. SU-8 panels are patterned using conventional photolithography. (ii) PCL is deposited in hinge gaps. (iii) Structures are lifted off via dissolution of a polyvinyl alcohol (PVA) layer in water and self-assembly occurs above 50° C. In FIG. 1b, schematic diagrams i-iii demonstrate self-folding of a cubic container according to an embodiment of the current invention. External "locking" hinges in pairs are mating edges in the folded configuration. FIG. 1c is a video capture sequence (over 15 seconds) showing a 1-mm/side, six-windowed polymeric microcontainer self-folding at 60° C. according to an embodiment of the current invention.

FIG. 2a is a fluorescent image of a group of 1 mm/side closed faced polymeric microcontainers according to an embodiment of the current invention. FIG. 2b is a fluorescent image of 500 μm/side polymeric cubes with isotropic porosity. The pores are square shaped with dimensions of 73×73 μm, arranged in 3×3 arrays on each face. FIG. 2c is an optical image of a 1-mm/side polymeric microcontainer with isotropic porosity. Each face is patterned with 8 µm-diameter round pores in a 20×20 array, as shown in the magnified inset. FIG. 2d is a schematic illustration showing self-assembly and optical curing of self-folded cubic containers into 3D scaffold-like geometries according to an embodiment of the current invention. The containers are functionalized with a hydrophobic adhesive and agitated in a vial of water, to form an aggregate, which is then fixed in place by curing the adhesive using UV light. FIG. 2e is a bright field image of a 2×2 mm polymeric cube-array.

FIG. 3a is a fluorescence image of a group of 1 mm sized, non-porous polymeric containers. FIG. 3b is a fluorescence image of 500 µm sized polymeric cubes with isotropic porosity. The pores are square shaped with dimensions of 73×73 µm and are precisely arranged in a 3×3 array on each face. FIG. 3c is a bright-field image of a 500 µm sized polymeric container with isotropic porosity. Here, each face has five precisely patterned 125 µm-diameter, circular-shaped pores. FIG. 3d is a bright-field image of a 1 mm sized polymeric container with 8 µm diameter circular-shaped pores in a 20×20 array. FIG. 3e is a bright-field image of a 1 mm sized container with a single square 500 µm pore and with a single microbead encapsulated within. FIG. 3f is a fluorescence image of a self-folded 500 µm sized dodecahedron with a single 250 µm sized pentagonal pore on each face.

FIG. 4a shows multicolored micro-beads encapsulated in six-faced polymeric containers, with 500 µm square pores in the center of each face. FIG. 4b shows a bright-field image of a gelatin-coated polymeric container retaining encapsulated Trypan blue dye. The dye-loaded container was coated with a ~2 µm thick layer of gelatin from bovine skin, type B (Sigma Aldrich) on all sides by pipetting 3 mL of 2% gelatin solution on a Teflon-coated glass slide and agitating the container in the solution. FIG. 4c is a bright-field and FIG. 4d a fluorescence z-plane stack image of stained fibroblast cells encapsulated within a non-porous polymeric container. The green color indicates that the cells are alive. FIGS. 4e and 4f are bright-field and fluorescence images of Artemia eggs encapsulated in porous polymeric cubes. Individual eggs are circled on the image.

FIG. 5a is a bright-field image of pancreatic cells in a container immediately following encapsulation by tumbling. FIG. 5b is a fluorescence image of stained pancreatic cells 60 h following encapsulation. FIG. 5c is a bright-field image and FIG. 5d is a fluorescence image of pancreatic cells 180 h following encapsulation.

FIG. 6a shows bright-field and fluorescence images of Syto 9 stained E. coli encapsulated within a polymer container, 24 h after encapsulation. FIG. 6b shows bright-field time-lapse images of bacteria within a polymeric container, taken at intervals of zero, 4 and 15 h following encapsulation by tumbling. Also shown is a plot of the number of bacteria vs. culture time following encapsulation. The Roman numeral labels on the graph correspond to the time points at which the images were obtained.

FIG. 8a is a conceptual schematic of a conventional 2D microwell array and FIG. 8b is an example of a 3D microwell array according to an embodiment of the current invention. FIGS. 8c-8f show numerical simulations and comparison of cell viability in a single 2D versus 3D porous microwell with cylindrical geometry. Spatial variation of viable (marbled) and necrotic (cross hatched) cells within a microwell with FIG. 8c one porous face (a conventional 2D microwell) and FIG. 8d a microwell with porosity on all faces except the one at the bottom according to an embodiment of the current invention. The $O_2$ concentration outside the microwell is color coded as per the legend in the figure and the arrows represent the diffusive flux of $O_2$ in the medium surrounding the microwell. FIG. 8e is a plot of the fraction f of the volume of the microwell where the $O_2$ concentration is larger than the threshold concentration $C_{cr}$ (0.1 µM) required for viable β-TC-6 cells versus the porosity of each face. The three panels correspond to cylindrical microwells with heights (or diameters) of 500, 250 and 100 µm. The regions shown in solid (3D microwell) and hatched (2D microwell) are bounded by low and high literature values of consumption rates (J. L. Dulong and C. Legallais, Biotechnol. Bioeng., 2007, 96, 990-998; P. Buchwald, Theor. Biol. Med. Modell., 2009, 6, 5). FIG. 8f is a plot of f versus both the cell density and $O_2$ consumption rate within a microwell with a height (or diameter) of 500 µm and wall porosity φ=2.3%. The intersection of the dotted line in the plot corresponds to the parameters used in determining the spatial variation of viable cells shown in FIGS. 8c and 8d.

FIG. 10a is an optical image of a 65 µm thick SU-8 holder with recessed slots and a 3×3 array of microwells positioned with their open faces oriented upwards according to an embodiment of the current invention. Optical images of ordered 3D microwell arrays on both FIG. 10b flat and FIG. 10c curved surfaces. The number 3 and letter D are spelt out to highlight versatility in the spacing and positioning offered by this arraying technique. All scale bars are 500 µm.

FIG. 16a illustrates a hollow container with porous walls filled with a chemical (or dye) that will release the chemical via diffusion. FIG. 16b shows an example of variation of dye concentration outside of the container as a function of time. The exact nature of this variation is determined by the container geometry (size and shape) and its porosity. FIG. 16c shows timing of chemical release (its start, peak and end as defined in FIG. 16b) for containers presented as a function of the pore size. Containers were assumed to be cubic 500 µm in size. The graph also illustrates the procedure for arranging different generations of boxes in time. This way one can "preprogram" when a given pixel would become visible and when it once again fades away. FIG. 16d shows parameters that characterize chemical release plotted as a function of container height (or volume since the cross-section of the container is kept constant at 500 µm). In the first approximation, the start and peak of chemical release do not depend on the container volume, only the duration of chemical release does.

FIG. 17a provides photos of containers with various time release characteristics which were used for the animation. FIG. 17b shows numerical simulations of dye concentration as a function of time for the containers shown in FIG. 17a. FIG. 17c is a diagram showing the position of various boxes used for the animation. FIGS. 17d-17f are actual animation frames.

FIGS. 18a and 18b show containers with one pore per face which were used in the experiment. FIG. 18c is a schematic cross-section of our experimental setup. Glass slides are used to hold 2D patterns of containers in place. The slides are placed on a PDMS sheet to prevent them from moving. The containers are covered with viscous agarose gel which serves as the medium for diffusion. FIG. 18d is a top view 2D pattern in the shape of a cross created with containers similar to the ones shown in FIGS. 18a and 18b. Here the containers with 100 µm pore on 5 faces of the cube are positioned within the blue rectangle while containers with one 25 µm pore are positioned within the areas marked with yellow and green rectangles. FIG. 18e shows that four minutes after the containers are positioned in the gel the containers with 100 µm pores have already released a considerable fraction of the dye they contained creating a visible line that is parallel to the blue region of FIG. 18d. FIG. 18f shows that approximately 50 minutes later the containers with the larger pores have almost finished their chemical release while the containers with smaller pores still release chemicals.

FIG. 19a illustrates that containers can be arranged within arrays by inserting them into a crate-like structures or printed on substrates. FIG. 19b shows that alternatively, they can be printed on flat substrates by a method similar to ink-jet printing.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Figures 1A, 1B, 1C:
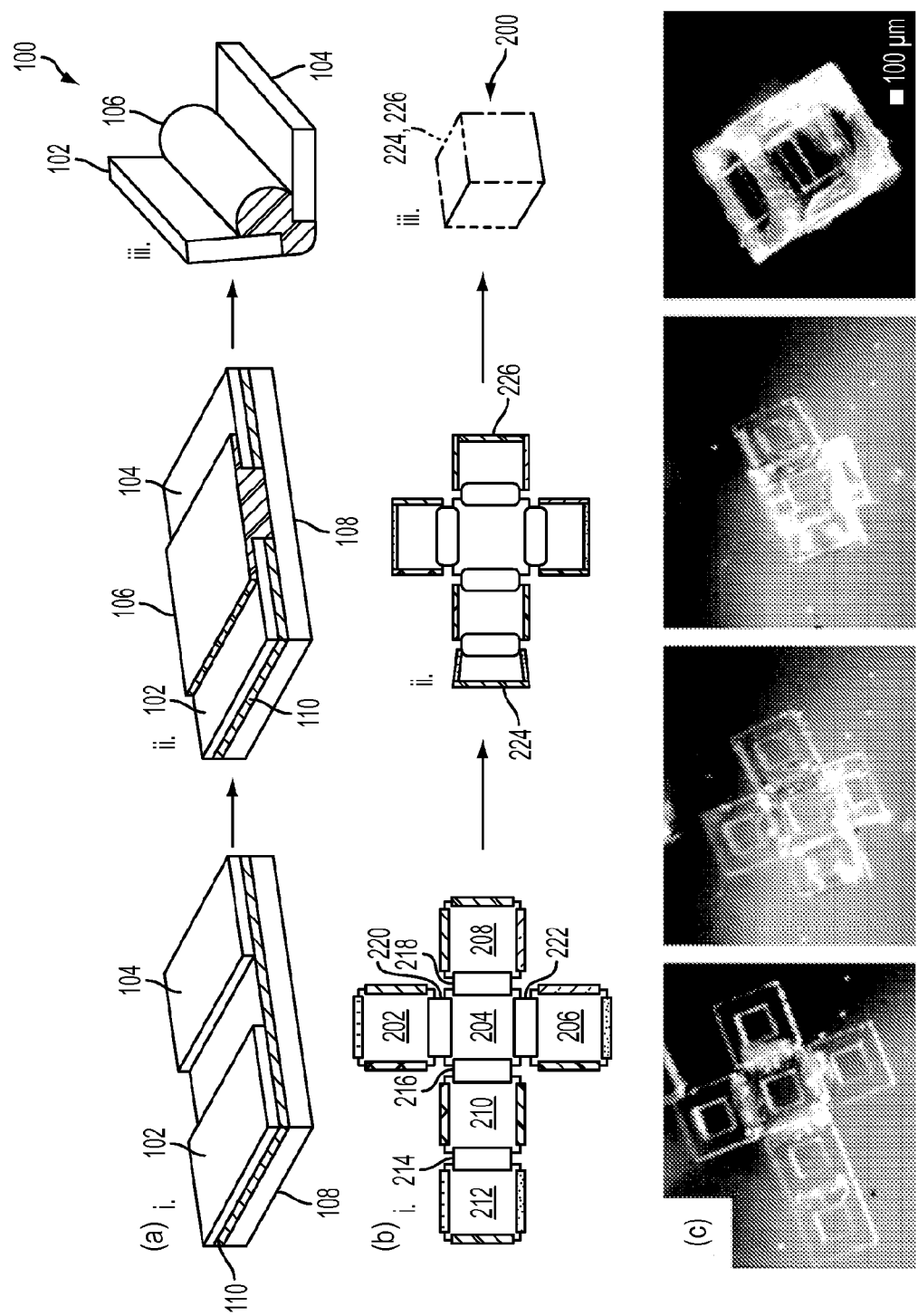
FIGS. 1a-1c illustrate a representative fabrication process flow and self-folding sub-centimeter structure for an example of polymeric microcontainers according to an embodiment of the current invention.

Some embodiments of the current invention are directed to an array structure that comprises a plurality of containers arranged in a predetermined pattern. Each container of the plurality of containers has a maximum outer dimension that is less than about 1 cm and a substantially predetermined porosity. FIGS. 1a-1c show some examples of containers that can be used to form array structures according to some embodiments of the current invention. Containers can be constructed according to the methods of International Application No. PCT/US2011/034200 assigned to the same assignee as the current application, the entire contents of which are incorporated herein by reference. However, the general concepts of the current invention are not limited to only the self-folding structures of this PCT application. For example, containers could be constructed according to the methods described in International Patent Application No. PCT/US2009/036391, the entire contents of which are incorporated herein by reference, or other available methods. In some embodiments, the containers can be polyhedral containers. However, the general concepts of the invention are not limited to only polyhedral containers. For example, the container can be spherical, cylindrical or other shapes according to some embodiments of the current invention.

Over the last several years, self-folding methods for transforming lithographically patterned 2D templates into hollow micro-containers have been developed (B. Gimi, et al., *Biomed. Microdev.* 2005, 7, 341-345 (2005); T. G. Leong, et al., *Langmuir* 23:8747-8751 (2007)). These containers also feature precise patterning of pores in all three dimensions. Many conventional micro-containers have a primarily metallic composition to facilitate photolithographic patterning and wet etching. Some metallic containers interact with electromagnetic fields to enable remote heating (H. Ye, et al., *Angew. Chem.* 46:4991-4994 (2007)) and imaging (B. Gimi, et al., *Cell Trans.* 16:403-408 (2007)), and containers coated with gold have been shown to be nontoxic to cells. Containers described in PCT/US2011/034200 can also provide biodegradability and optical transparency, for example. Polymers also remain the material of choice in constructing devices for cell encapsulation therapy, tissue engineering and drug delivery (S. Prakash, H. Soe-Lin, *Trends Biomat. Artif. Organs,* 18:24-35 (2004)).

According to some embodiments of the current invention, self-folding micro-containers can be fabricated with all-polymeric compositions and can be used to encapsulate beads, chemicals, live cells and microorganisms, for example. Containers according to some embodiments of the current invention can be optically transparent, which facilitates easy viewing of encapsulated cells and organisms. They can also be comprised of materials commonly used in bioMEMS and drug delivery, including, but not limited to, SU-8 panels and biodegradable poly ($\epsilon$-caprolactone) (PCL) hinges, for example.

SU-8 is a biocompatible, photosensitive and mechanically stable epoxy-based polymer that is commonly used to fabricate microfluidic (see P. J. Hung, et al., *Lab Chip* 5:44-48 (2005)) and drug delivery devices (see S. L. Tao, et al., *Nat. Protocols* 1:3153-3158 (2007)). PCL is biocompatible and has adequate mechanical strength, which allows for its use in a range of biomedical microdevices. See D. K. Armani, C. Liu, *J. Micromech. Microeng.* 10:80-84 (2000); A. G. A Coombes, et al., *Biomaterials* 25:315-325 (2004); B. W. Tillman, et al., *Biomaterials* 30:583-588 (2009). PCL also is a biodegradable polymer, so that when it is used as a hinge material in a larger device, biodegradation can cause the device to come apart over time. This concept of self-disintegration has been explored previously in biomedical devices, specifically in the M2A patency capsule (see A. J. Postgate, et al., *Dig. Dis. Sci.* 53:2732-2738 (2008)), a self-disintegrating wireless, video capsule based swallowable device, which is held together by paraffin plugs that typically begin to dissolve after 30 hours following ingestion. The capsule's self-disintegration causes it to be more easily excreted after it has achieved its function. However, the broad concepts of the current invention are not limited to these particular examples.

FIG. 1a is a schematic illustration of a sub-centimeter structure 100, and methods of producing the sub-centimeter structure 100, which can be used as containers for array structures according to some embodiments of the current invention. However, the containers are not limited to only this particular example. The sub-centimeter structure 100 has a first structural component 102, a second structural component 104 arranged proximate the first structural component 102, and a joint 106 connecting the first and second structural components 102, 104. The joint 106 is a material that has a first phase that is substantially rigid to hold the first and second structural components 102, 104 in a substantially rigid configuration while the material of the joint 106 is in the first phase. The material of the joint 106 has a second phase such that the joint 106 is at least partially fluid to allow the first and second structural components 102, 104 to move relative to each other while the material is in the second phase. The joint 106 interacts with the first and second structural components 102, 104 while the material is in the second phase to cause the first and second structural components 102, 104 to move relative to each other.

In the example of FIG. 1a, the structural components 102 and 104 are formed on a substrate 108, for example by a lithographic process. However, the broad concepts of the current invention are not limited to only providing the structural components by lithographic processes. In this example, there is a sacrificial layer of material 110 between the structural components 102, 104 and the substrate 108. In this example, once the structural components 102 and 104 are provided and a joint 106 connects the structural components 102 and 104, the substantially two-dimensional structure can be "lifted off" the substrate by at least partially removing the sacrificial layer. The sacrificial layer can be dissolved or made to undergo a phase change such as melting, for example. In this example, after the structure is lifted off the substrate, the joint 106 is exposed to heat such that it at least partially melts. In this example, the surface tension of the material of the joint 106 causes the structural components 102 and 104 to move relative to each other due to the "beading up" of the material of the joint more on one side of the structure 100 than the other. Consequently, the sub-centimeter structure "self-assembles" into an L-shaped structure in this example.

The term "self assemble" is being used to distinguish from the case in which each structural component is individually positioned into the final configuration. According to an embodiment of the current invention, many structures can self-assemble in parallel by subjecting them all to heat at the same time. Thus they self assemble once the proper environmental conditions, such as temperature, are realized. When the sub-centimeter structure 100 self-assembles, it can be cooled such that the joint 106 again becomes rigid to hold the sub-centimeter structure rigidly together. The joint 106 is sometimes referred to as a hinge. The term hinge is not to be construed as always allowing movement of the structural components. Similarly, the term "joint" is intended to cover both a rigid joint, or a joint that compels movement of structural components. The term joint as used herein is intended to include the term hinge.

The structure is referred to as a sub-centimeter structure since there may be some applications in which relatively large structures, up to about 1 cm for example, may be desired. However, in other cases it may be desirable for the structure to be a sub-millimeter structure, or even a sub-micron structure.

According to some embodiments of the current invention, a plurality of structural components and a plurality of joints can be arranged such that the sub-centimeter structure is an enclosing structure in a configuration to provide enclosing containers according to an embodiment of the current invention. FIG. 1b is a schematic illustration of an example of a container 200 according to an embodiment of the current invention. The container 200 is cube-shaped "box" in this example. The container 200 has six structural components 202-212 and five joints 214-222. Also, pairs of edges, such as edge 224 and 226 can include material which will result in the overlapping edges (e.g., 224 with 226) to become joined or fastened together. In some embodiments, the edges, such as edges 224 and 226, can be the same material as the joints 214-222. However, different materials and different locking structures can be used according to other embodiments of the current invention. In some embodiments, the structural components, such as structural components 202-212, will be referred to as panels or sides. However, the structural components are not limited to only "panel-like" structural components.

FIG. 1c shows images of an actual sub-centimeter container corresponding to the schematic illustration of FIG. 1b. In this example, the fabrication process included three steps. Briefly, in the first two steps, 2D templates comprising SU-8 square panels connected by PCL hinges were patterned using a combination of photolithography and lift-off deposition on a poly(vinyl alcohol) (PVA) sacrificial layer. Any polymeric or gel-based material can be used in place of SU-8 for the panels provided the polymeric or gel-based material: (a) is patternable; (b) is sufficiently rigid so as not to collapse during folding; and (c) an appropriate sacrificial layer that provides dissolution selectivity can be found.

PCL hinges were deposited in alignment with the SU-8 panels. For the hinge material, there was the additional constraint that the material can be liquefied at a low temperature; for example, PCL softens at 50° C. and has a melting point of 58° C. The 2D SU-8 panels interconnected with PCL hinges were then released from the substrate by dissolution of the PVA sacrificial layer in water. The 2D templates spontaneously folded into three-dimensional (3D) cubes in water, PBS solution and cell media upon heating above 50° C. In principle, using the presently disclosed methods and materials, any microscale, three-dimensional, polyhedral structure having precisely patterned faces can be constructed. In representative, non-limiting embodiments, such as the example of FIG. 1c, the panels are square. One of ordinary skill in the art upon review of the presently disclosed subject matter would recognize that panels having other geometries are suitable for use with the presently disclosed methods and materials. Also, each panel in the example of FIG. 1c has a window-like through hole to permit the flow of fluids and small particles therethrough. These will also be referred to as pores.

As used herein, the term "polyhedral" refers to of or relating to, or resembling a polyhedron. The term "polyhedron" refers to a three-dimensional object bounded by plane polygons or faces. The term "polygon" refers to a multisided geometric figure that is bound by many straight lines, including, but not limited to, a triangle, a square, a pentagon, a hexagon, a heptagon, an octagon, and the like. For example, the presently disclosed containers, in some embodiments, can be a cube. A cube is a three-dimensional object bounded by six square faces or sides, with three sides meeting at each vertex, i.e., a corner.

One of ordinary skill in the art also would appreciate that the presently disclosed containers also can be fabricated on the nanoscale, e.g., having a dimension from about 1 nm to about 999 nm. In some embodiments the container is an enclosing structure in a configuration that has a maximum outer dimension of at least 10 nm and less than 10 mm. In further embodiments the container is an enclosing structure in a configuration that has a maximum outer dimension of at least 10 nm and less than 1 mm. In still further embodiments the container is an enclosing structure in a configuration that has a maximum dimension of at least 10 nm and less than 1 µm.

In illustrative embodiments, self-folding occurred within a one-minute time frame (see FIGS. 1b-1c). The self-folding phenomenon is thought to be driven by a minimization of surface tension of the liquefying PCL hinges. However, the invention is not limited by any particular theory. At temperatures exceeding 50° C., the solid PCL in the hinge gaps transitioned from a white, opaque solid state to a transparent softened state, and the panels rotated upwards as a result of a torque generated by the phase change (FIG. 1c). In representative embodiments, the presently disclosed hinge design used external "locking" hinges bordering the 2D panels (shade grey in FIG. 1b, e.g., 224 and 226), which is thought to play an important role in achieving self-correction in the container's faces to yield a well-formed cube structure during the self-folding step of the fabrication process.

Under circumstances in which the hinge gap had a high volume of PCL, any excess was retained within the container and reduced the encapsulation volume. As compared to self-folding metallic containers, a greater degree of self-correction was observed during self-folding of the presently disclosed containers due to the mechanical flexibility of the SU-8 panels. The hinges exhibited considerable reflow when heat was applied until the container reached a state of lowest free energy. Faces were observed to self-correct by about 10 degrees to about 15 degrees after making orthogonal contact with adjacent faces until the distribution of molten PCL in the edges of the microcontainers equalized in a low-energy state. Upon cooling, the PCL solidified and the cubes were sealed. An advantage of the presently disclosed self-folding process is that it provides for parallel fabrication of a plurality of containers, although yields vary depending on the method used for depositing and patterning the hinges.

Figures 2A, 2B, 2C, 2D, 2E:
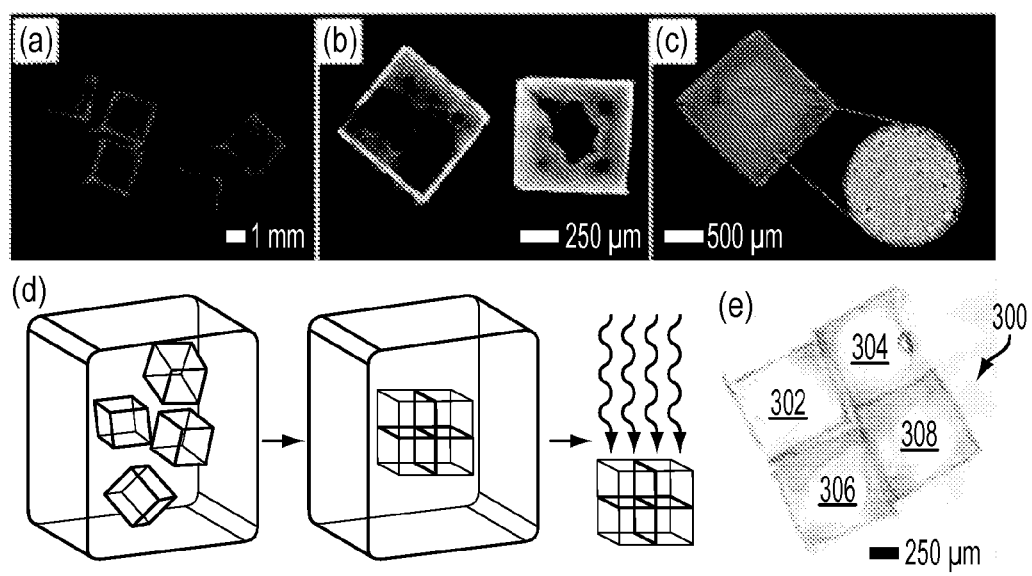
FIGS. 2a-2e demonstrate the versatility and 3D self-assembly of multiple containers according to some embodiments of the current invention.
Figures 3A, 3B, 3C, 3D, 3E, 3F:
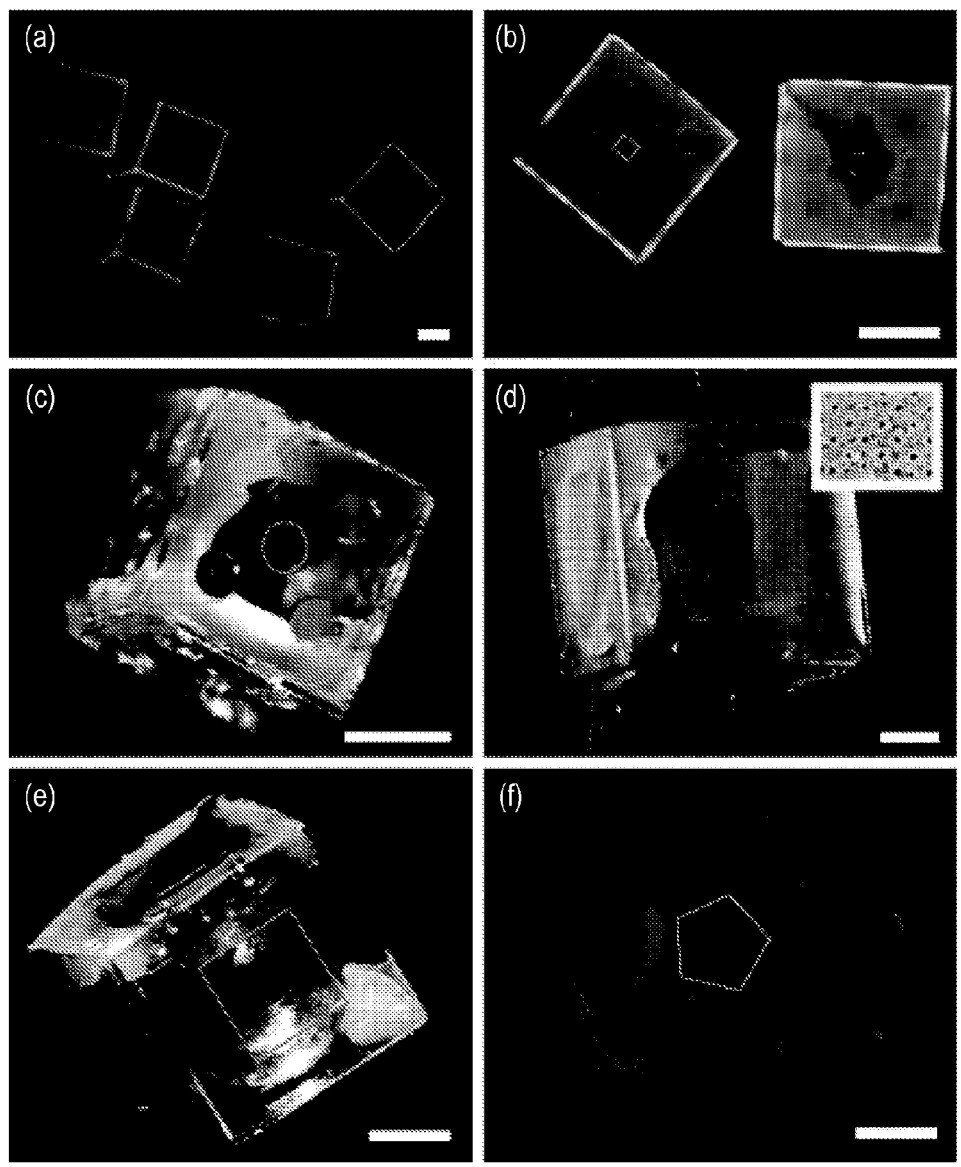
FIGS. 3a-3f show some examples of self-folding of multiple containers and versatility in polyhedral shape, size and precise porosity in all three dimensions according to some embodiments of the current invention. The lithographically patterned pores are outlined on the images and the scale bar is 250 µm long.

FIGS. 2d-2e illustrate an example of an array structure 300 according to an embodiment of the current invention, as well as a process of forming the array structure 300. The array structure includes a plurality of containers (302, 304, 306, 308) arranged in a predetermined pattern. Each container (302, 304, 306, 308) has a maximum outer dimension that is less than about 1 cm. Each container (302, 304, 306, 308) also has a substantially predetermined porosity. In other embodiments, in addition to cubic containers, larger structures for scaffolding applications also can self assemble. In such embodiments, a plurality of polymeric containers can be functionalized with a hydrophobic adhesive, for example (see J. Tien, et al., *J. Am. Chem. Soc.* 120:12670-12671 (1998); Z. Y. Gu, et al., *Langmuir* 20:11308-11311 (2004)). The containers were placed in a vial of water and shaken gently to form aggregates based on the surface energy minimization of the exposed hydrophobic area. These structures were then fixed in place by curing the adhesive using ultraviolet light. It is also possible to pattern a wide range of porosities with a high level of control within individual units and thereby precisely engineer the porosity of the overall array structure 300, which can be a scaffold in this example.

FIGS. 3a-3f show some further examples of containers that can be used for array structures according to some embodiments of the current invention. For example, the polyhedron container sizes can have a maximum outer dimension that is less than 1 cm and greater than 1 nm according to an embodiment of the current invention. In other embodiments, the polyhedron container sizes can have a maximum outer dimension that is less than 100 µm and greater than 10 nm, for example. In other embodiments, the polyhedron container sizes can have a maximum outer dimension that is less than 10 µm and greater than 100 nm, for example. In other embodiments, the polyhedron container sizes can have a maximum outer dimension that is less than 1 μm and greater than 100 nm, for example.

The pore shapes can be selected, according to the desired application. For example, the pore shapes can be, but are not limited to, square or round shapes. The pores can be considered to have an effective size for some particular applications. The pore densities can also be predetermined by constructing the containers. In one extreme limit, the pore density can approach 0%. At the other extreme the pore density can approach 100%. In one embodiment, the pore density can be at least 10% and less than 90%. In another embodiment, the pore density can be at least 20% and less than 80%. In another embodiment, the pore density can be at least 30% and less than 70%. In another embodiment, the pore density can be at least 40% and less than 60%. The pore sizes, shapes and densities can be the same, or can be different on each of the sides of the container. Furthermore, the containers of an array structure according to some embodiments of the current invention can all be substantially the same, or some or all can differ in number of sides, sizes, pore sizes and shapes, and pore densities, for example. Also, the materials of the individual containers of the array structure 300 can all be the same, or some or all could differ in their constituent materials.

Figures 4A, 4B, 4C, 4D, 4E, 4F:
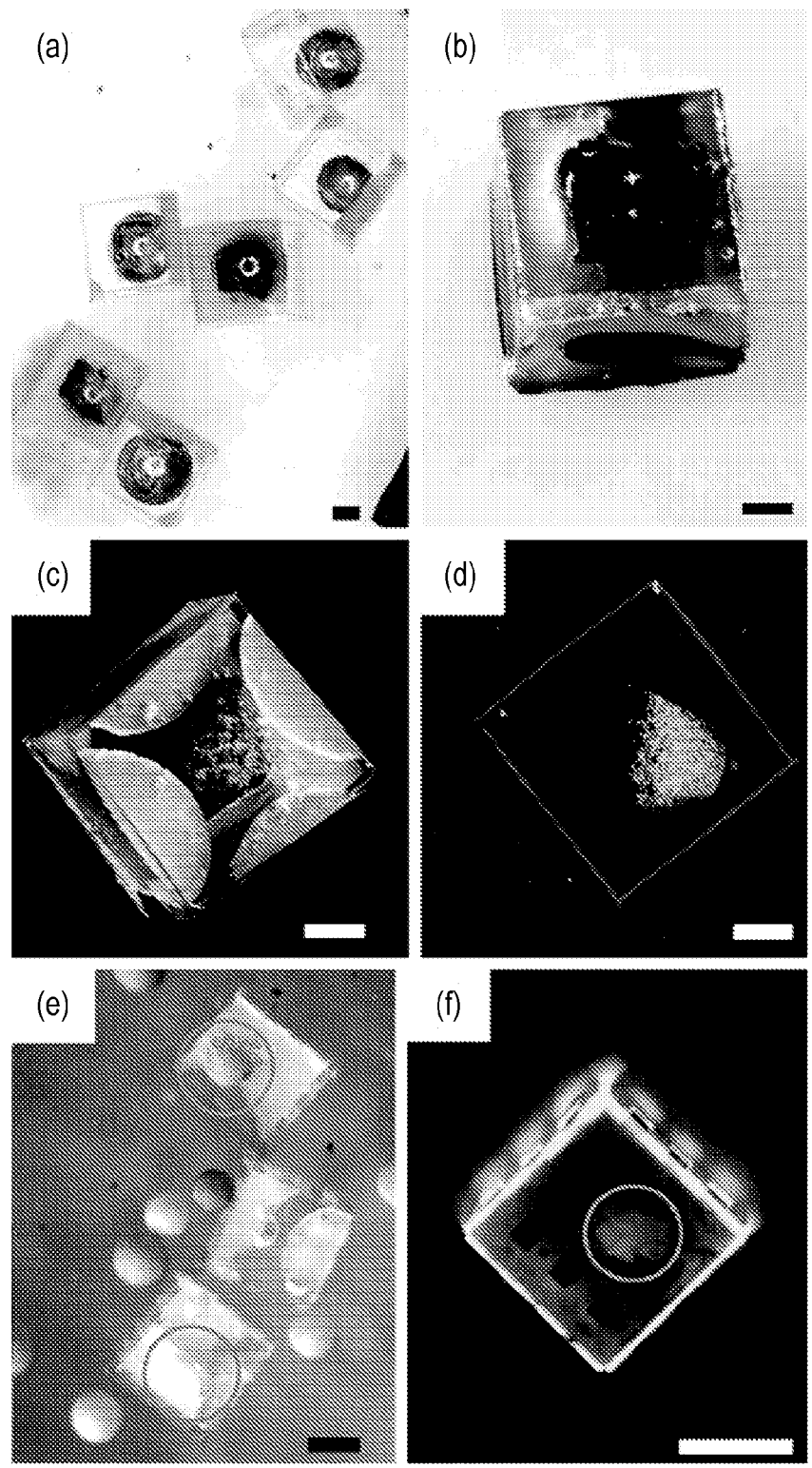
FIGS. 4a-4f show examples of encapsulation of beads, chemicals, cells and Artemia eggs according to an embodiment of the current invention. The scale bar is 250 µm long.
Figures 5A, 5B, 5C, 5D:
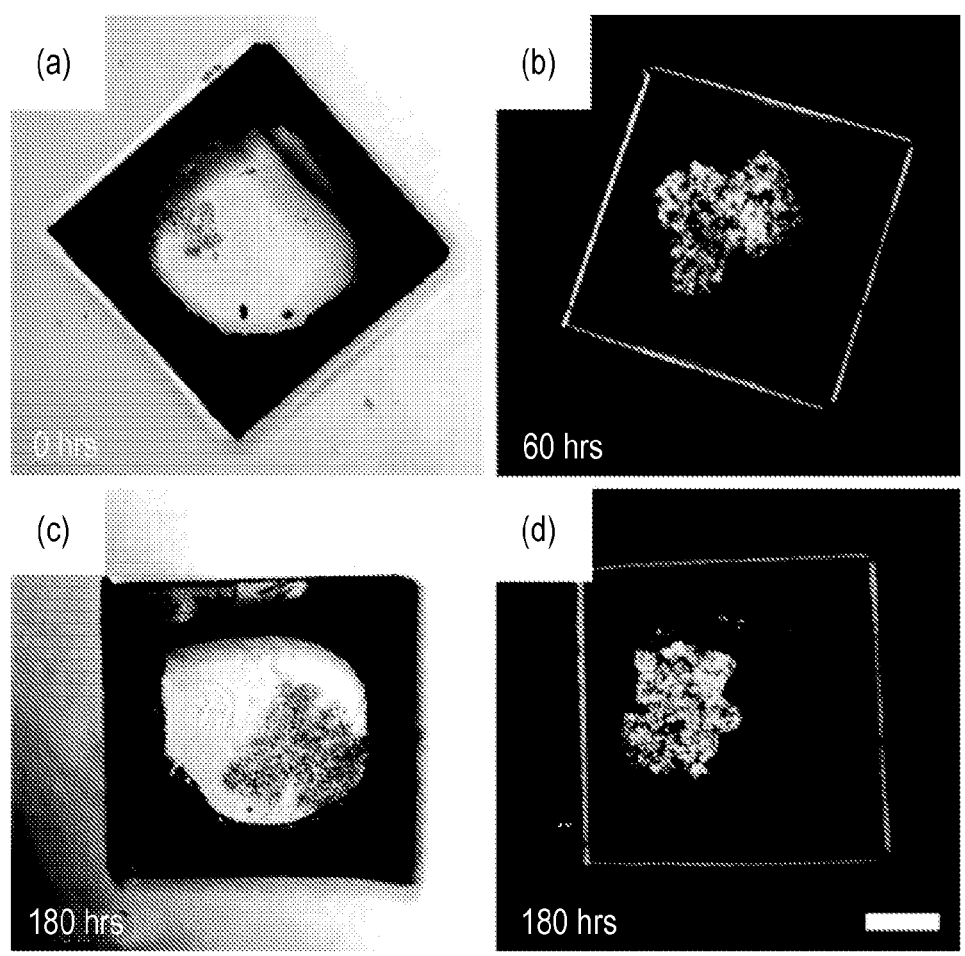
FIGS. 5a-5d shows multi-day time-lapse images of pancreatic cells encapsulated in a polymer container according to an embodiment of the current invention. The scale bar is 250 µm long.
Figures 6A, 6B:
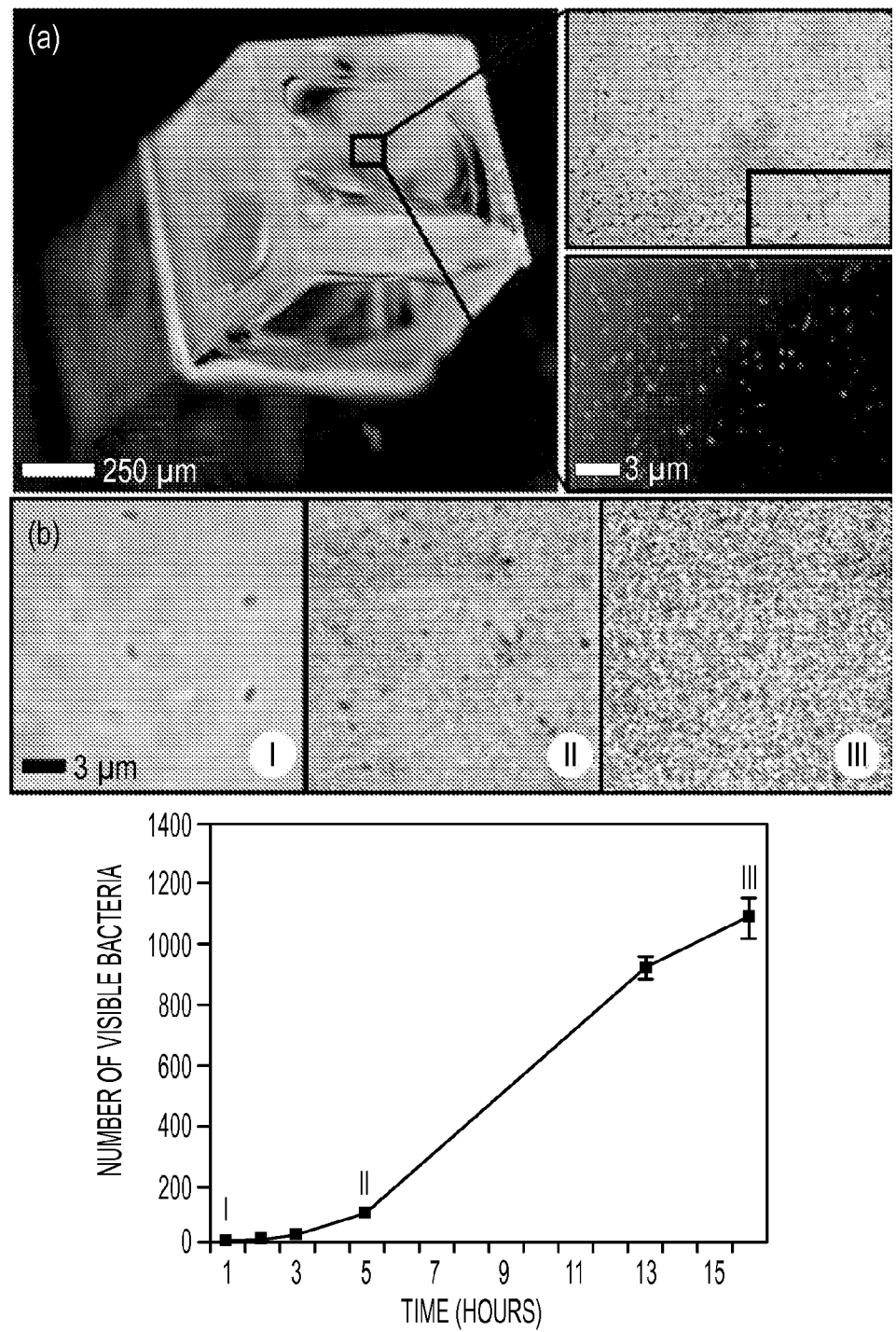
FIGS. 6a and 6b is an example of bacterial encapsulation and culture according to an embodiment of the current invention.

The containers can encapsulate a wide range of materials and/or organisms. For example, representative containers were loaded with beads (FIG. 4a), chemical dyes (FIG. 4b), fibroblast cells (FIGS. 4c-4d), brine shrimp (*Anemia salina*) eggs (FIGS. 4e-4f), pancreatic cells (FIGS. 5a-5d) and bacteria (FIGS. 6a-6b) (*E-coli*) (see also, A. Anum, et al, Biomed Microdevices (2011) 13:51-58, the entire contents of which are incorporated herein by reference). Containers could be self-loaded by assembling them in the presence of cargo in a manner similar to loading vesicles or liposomes. See A. Fritze, et al., *Biochim. Biophys. Acta—Biomembranes* 1758:1633-1640 (2006); T. G. Leong, et al., *Lab Chip* 8:1621-1625 (2008).

In experiments with PCL hinged containers, however, self-loading required heating above 50° C., which is lethal for many kinds of cells. Accordingly, for live cell loading, folded containers with small (approximately 5 μm to 10 μm wide) gaps within the hinges were tumbled in media with a high cell concentration. Cells entered the container through the gaps and live cells could be imaged within the container (FIGS. 5a-5d).

Further, one feature of containers for some applications is that they can be optically transparent, which allows imaging of encapsulated contents using both bright field and fluorescence imaging. Cells could be imaged in a non-invasive manner. Polymeric containers of varying sizes with encapsulated microbeads, cells, eggs, and dyes were imaged using optical microscopy (FIGS. 4a-4f), without damage to the contents of the containers.

Porosity in all three dimensions of the containers allows enhanced diffusion with the surrounding media. Some embodiments of array structures can be formed by self-assembly methods, for example. Some embodiments can provide miniaturized multi-well growth chips for microorganism culture, high-throughput screening and building bacterial communities. See C. J. Ingham, et al., *Proc. Natl. Acad. Sci. USA*, 104:18217-18222 (2007); D. B. Weibel, *Proc. Natl. Acad. Sci. USA*, 105:18075-18076 (2008). In some embodiments, the containers resemble miniaturized micro-Petri dishes or multi-well plates with enhanced 3D diffusion and the potential for in situ imaging of encapsulated contents. Dye loaded containers can either be uncoated or further coated with nanoporous gels, such as gelatin, to slow down the rate of dye release. Depending on the porosity of the containers and the type of coating used, it would be possible to tune chemical release over a wide time scale. The use of PCL as hinges also offers the possibility for biodegradability and long-term release of encapsulated contents. PCL is known to be biodegradable via hydrolysis of its ester linkages and by enzymes, see G. E. Wnek, G. L. Bowlin, *Encyclopedia of Biomaterials and Bioengineering*, Informa Healthcare, London, UK, 2nd ed., 2008, vol. 1, pp. 8-31; hydrolytic degradation is accelerated at high or low pH.

Figure 7:
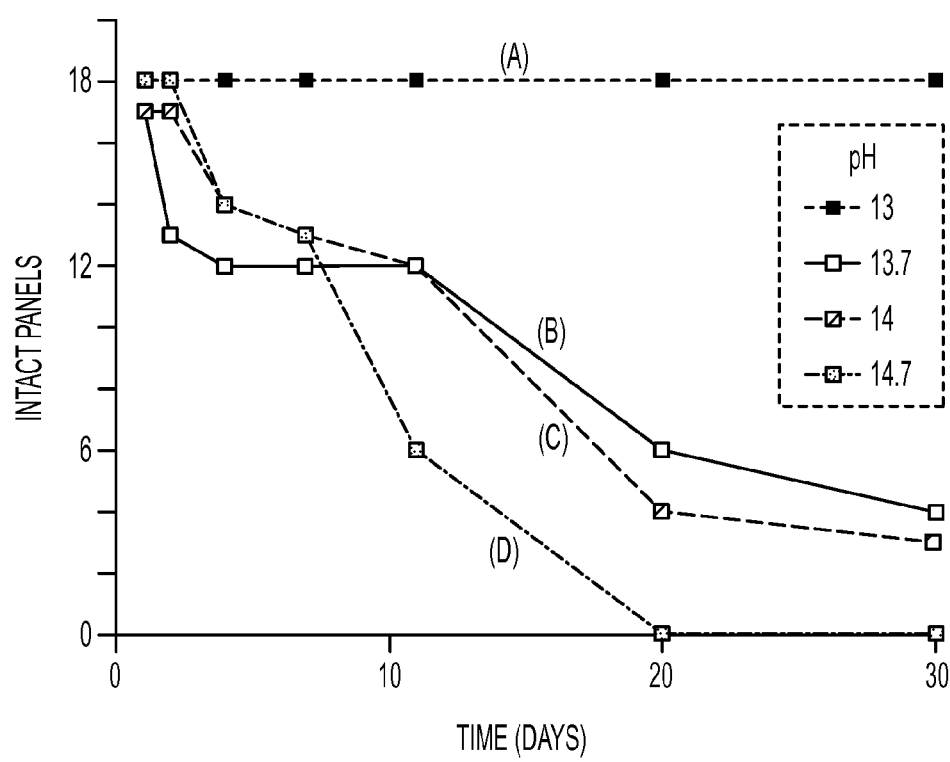
FIG. 7 is a plot of the PCL hinge degradation rates at different pHs.

According to some embodiments of the current invention, biodegradation of the containers in PBS-based media was monitored using an accelerated test with variable high pH (FIG. 7). The presently disclosed results are in agreement with published literature in that containers degrade faster in more alkaline media. See C. X. F. Lam, et al., *Biomed. Mater.*, 3:034108-22 (2008); J. Pefia, et al., *I Biomed. Mater. Res.* 76A:788-797 (2006). The presently disclosed hinges, however, degraded more rapidly (on the order of 30 days for pH>13) as compared to published data. This faster degradation rate can be attributed to a much smaller volume of PCL within the hinges. However, the current invention is not limited to whether or not this theory is correct. Nevertheless, the utility of PCL hinges within the containers demonstrate the applicability of constructing a self-disintegrating container.

Numerous studies have shown that PCL degradation can be carefully timed and controlled through its copolymerization with other biocompatible materials, such as collagen and chitosan. See B. W. Tillman, et al., *Biomaterials* 30:583-588 (2009); G. E. Wnek, G. L. Bowlin, *Encyclopedia of Biomaterials and Bioengineering*, Informa Healthcare, London, UK, 2nd edn, 2008, vol. 1, pp. 8-31; Y. Wan, et al., *Polym. Degrad. Stab.* 93:1736-1741 (2008). This copolymerization strategy can be utilized to precisely engineer the kinetics of hinge degradation.

As used herein, the terms "container," "biocontainer," and "microscale encapsulant" refer to a three-dimensional object, i.e., a receptacle, having a hollow interior or an interior capable of containing substances.

In some embodiments, the containers are available as vessels for encapsulation of materials or substances, including, but not limited to, drugs or other therapeutic agents, biological media, including cells and tissues, gels, and polymers, including natural or synthetic polymers, such as proteins (polymer of amino acids) and cellulose (polymer of sugar molecules), which subsequently can be released in situ. See, e.g., U.S. Patent Application Nos. US2007/0020310 A1, published Jan. 25, 2007, and US2009/0311190 A1, published Dec. 17, 2009, each of which is incorporated herein by reference in its entirety.

Such materials or substances can be contained within, loaded into, or otherwise associated with, e.g., directly bound, adhered, or attached through a linker to, the containers. The materials or substances can subsequently be released from the containers. In some embodiments, the release can be a slow or time-elapsed release to provide a pre-determined amount of the material or substance to a subject over a period of time. Such embodiments include both in vitro and in vivo applications. Accordingly, materials or substances encapsulated by the presently disclosed containers can be delivered to a specific target or generally administered to a subject.

In some embodiments, the presently disclosed containers can be loaded with cells embedded in a gel. The term "gel" as used herein refers to an apparently solid, jelly like material formed from a colloidal solution. The term "colloid" or "colloidal" as used herein refers to a substance made up of a system of particles dispersed in a continuous medium. By weight, gels are mostly liquid, yet they behave like solids. The term "solution" refers to a homogeneous mixture of one or more substances (the solutes) dissolved in another substance (the solvent). The cells could be released by immersing the microstructure in an appropriate solvent.

In some embodiments, functional cells (e.g., pancreatic islet cells, neuronal PC12 cells) can be encapsulated for in vitro and in vivo release with or without immunosuppression. For example, the presently disclosed containers can be used to encapsulate and deliver insulin secreting cells for implantation in patients afflicted with diabetes and for placing tumor innocula in animal models where constraining cells within a small region is necessary, and for delivering functional PC12 cells, for example, to model neuronal differentiation.

The presently disclosed subject matter also includes a method of treating a disease, condition, or disorder in a subject in need of treatment thereof, the method comprising using an array structure that encapsulates a composition, wherein the composition is released through one or more pores within the containers into the subject in an amount sufficient to treat the condition.

In one embodiment of this method the condition is diabetes and the composition comprises one or more insulin-secreting cells.

As used herein, the term "therapeutic agent" refers to any pharmaceutical agent, composition, gene, protein cell, molecule, or substance that can be used to treat, control or prevent a disease, medical condition or disorder. The term "treat" or "treating" includes abrogating, substantially inhibiting, slowing or reversing the progression of a condition, substantially ameliorating clinical or symptoms of a condition, and substantially preventing the appearance of clinical or symptoms of a condition.

The amount of a therapeutic agent that results in a therapeutic or beneficial effect following its administration to a subject, including humans, is a "therapeutic amount" or "pharmaceutically effective amount." The therapeutic or beneficial effect can be curing, minimizing, preventing, or ameliorating a disease or disorder, or may have any other therapeutic or pharmaceutical beneficial effect.

The term "disease" or "disorder," as used herein, refers to an impairment of health or a condition of abnormal functioning. The term "syndrome," as used herein, refers to a pattern of symptoms indicative of some disease or condition. The term "injury," as used herein, refers to damage or harm to a structure or function of the body caused by an outside agent or force, which may be physical or chemical. The term "condition," as used herein, refers to a variety of health states and is meant to include disorders, diseases, or injuries caused by any underlying mechanism or disorder, and includes the promotion of healthy tissues and organs.

In some embodiments, the containers can further comprise a radio frequency tag, wherein the substance may be released upon the container's exposure to a pre-selected radio frequency. In a further embodiment, the substance can be released upon the container's exposure to electromagnetic radiation, which can be triggered remotely. The electromagnetic radiation capable of triggering the release can range from about 1 KHz to about 1 Peta Hz. In a further embodiment, the substance can be released upon the container's exposure to inductive heating. Such inductive heating can be triggered remotely.

In some embodiments, the containers also can comprise active electronic or semiconductor components including, but not limited to, transistors, sensors, actuators, light emitting diodes, photodiodes and solar cells. In yet other embodiments, the containers can be associated with a biosensor.

According to another embodiment of the current invention, the array structure can provide a micro-well array with three-dimensional perfusion (see also, C. Randall, et al, Lab Chip, 2011, 11, 127, the entire contents of which are incorporated herein by reference).

Since cells reside in 3D environments in vivo, it is necessary to develop platforms that enable the culture and study of aggregates of cells while providing adequate diffusion in all three dimensions. For example, cells have been suspended and cultured within gels (L. Kim, Y. C. Toh, J. Voldman and H. Yu, Lab Chip, 2007, 7, 681-694; S. Rhee, Exp. Mol. Med., 2009, 41, 858-865; D. R. Albrecht, G. H. Underhill, T. B. Wassermann, R. L. Sah and S, N. Bhatia, Nat. Methods, 2006, 3, 369-375; K. Bolt, Z. Upton, K. Schrobback, M. Ehrbar, J. A. Hubbell, M. P. Lutolf and S. C. Rizzi, Biomaterials, 2010, 31, 8454-8464) or on porous multilayered scaffolds (K. W. Lee, S. Wang, M. J. Yaszemski and L. Lu, Biomacromolecules, 2010, 11, 682-689; D. Gallego-Perez, N. Higuita-Castro, S. Sharma, R. K. Reen, A. F. Palmer, K. J. Gooch, L. J. Lee, J. J. Lannutti and D. J. Hansford, Lab Chip, 2010, 10, 775-782; A. Khademhosseini, R. Langer, J. Borenstein and J. P. Vacanti, Proc. Natl. Acad. Sci. U.S.A., 2006, 103, 2480-2487). Attempts have also been made to integrate channels within these materials to enable vasculature reminiscent of perfusion in 3D (N. W. Choi, M. Cabodi, B. Held, J. P. Gleghorn, L. J. Bonassar and A. D. Stroock, Nat. Mater., 2007, 8, 908-915; L. M. Bellan, S. P. Singh, P. W. Henderson, T. J. Porri, H. G. Craighead and J. A. Spector, Soft Matter, 2009, 5, 1354-1357). However, many existing methodologies provide limited control over geometric positioning of cell clusters such as can be achieved in an array as well as a lack of precise tunability of nutrient and waste diffusion in all three dimensions.

Culturing cells within present-day microwell arrays allows precise geometric positioning of cell clusters in culture and is a well-established practice in drug discovery, microbiology, tissue engineering and biotechnology (M. Charnley, M. Textor, A. Khademhosseini and M. P. Lutolf, Integr. Biol., 2009, 1, 625-634; B. Ma, G. Zhang, J. Qin and B. Lin, Lab Chip, 2009, 9, 232-239; D. Holmes and S. Gawad, Methods Mol. Biol. (Totowa, N.J.), 2010, 583, 55-80). This approach has been widely utilized due to ease of device fabrication, high throughput loading and compatibility with optical microscopy techniques (B. H. Weigl, R. L. Bardell and C. R. Cabrera, Adv. Drug Delivery Rev., 2003, 55, 349-377; P. J. Hung, P. J. Lee, P. Sabounchi, R. Lin and L. P. Lee, Biotechnol. Bioeng., 2004, 89, 1-8). Additionally, 2D microwells enable cells to be encapsulated and cultured in liquid media without the need for a gel. However, since conventional microwells are embedded in a flat substrate, they do not accurately mimic the natural cellular microenvironment due to a lack of 3D cues from the external media, thus generating physiologically compromised cells (R. C. Dutta and A. K. Dutta, Biotechnol. Adv., 2009, 27, 334-339). For example, due to limited access to the surrounding medium from only one opening (a single 2D interface) in traditional planar microwell arrays, hypoxic conditions resulting in decreased cell or tissue function have been reported (C. Rappaport, In Vitro Cell. Dev. Biol.: Anim., 2003, 39, 187-192; E. M. Metzen, J. Wolff, J.

Fandrey and J. Jelkman, Respir. Physiol., 1995, 100, 101-110; J. Malda, T. J. Klein and Z. Upton, Tissue Eng., 2007, 13, 2153-2162).

Figures 8A, 8B, 8C, 8D, 8E, 8F:
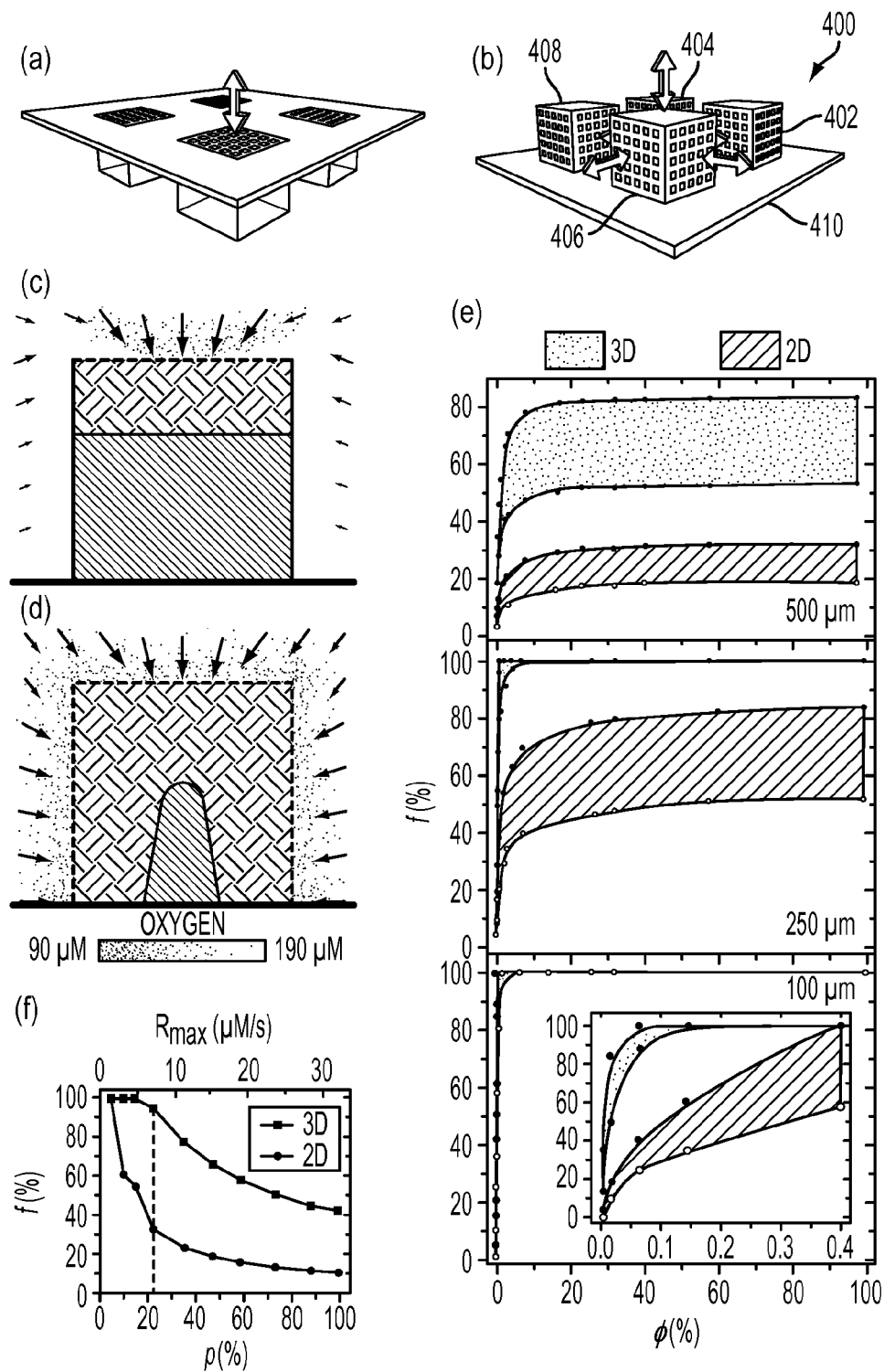
FIGS. 8a-8f illustrate some concepts of microarrays according to an embodiment of the current invention.

According to some embodiments of the current invention, we can extend the concept of a conventional microwell array (FIG. 8a) by creating arrays of microwells with externally exposed or porous sidewalls. FIG. 8b is an illustration of an array structure 400 according to an embodiment of the current invention that includes a plurality of containers (402, 404, 406, 408) attached to a substrate 410. The array structure 400 according to the embodiment of FIG. 8b provides and example in which the array structure provides a 3D microwell array. The 3D microwell array allows for the encapsulated cells to interact with their surroundings in all three dimensions (FIG. 8b) while retaining several of the attractive features of 2D microwell arrays described above.

A more quantitative understanding of the diffusion characteristics of these microwells and of expected differences in cell behavior in 2D and 3D can be observed from numerical simulations. We simulated microwell sizes of 100, 250 and 500 μm while systematically varying the face porosity. Here, we generated a model of $O_2$ consumption by encapsulated pancreatic β-cells. Our choice for simulating this cell line was motivated by its widespread use in diabetes therapy (E. S. Avgoustiniatos and C. K. Colton, in Bioartical Organs—Science, Medicine, and Technology, ed. A. Prokop, D. Hunkeler and A. D. Chemington, New York Acad Sciences, New York, 1997, pp. 145-167) and in research related to bioartificial pancreas development (J. L. Dulong and C. Legallais, Biotechnol. Bioeng., 2007, 96, 990-998; P. Buchwald, Theor. Biol. Med. Modell., 2009, 6, 5). The simulation parameters were chosen to correspond to experimental conditions while still remaining instructive. The individual 2D and 3D microwells were cylindrical in geometry and were placed in the bottom-center of the medium. Stationary solutions of the spatial variation of $O_2$ concentration were obtained by solving the diffusion equation with a reaction term, $$\frac{\partial c}{\partial t} + \nabla(-D\nabla c) = R.$$

Here, c is the $O_2$ concentration, D is the diffusion coefficient of $O_2$ in either the medium or through the cellular mass and R is the $O_2$ reaction rate per unit volume. For the boundary conditions, we assumed the $O_2$ concentration at the medium-air interface to be constant and equal to 0.2 mM (P. Buchwald, Theor. Biol. Med. Modell., 2009, 6, 5). The $O_2$ cellular consumption rate R for β-TC-6 cells was assumed to vary in accordance with Michaelis-Menten kinetics with a necrosis threshold step-function $\theta(c>c_{cr})$ such that, $$R = R_{max} \times \frac{c}{c + c_{mm}} \times \theta(c > c_{cr}).$$

Here, $c_{mm}$ is the Michaelis-Menten constant assumed to be 1.0 μM, $c_{cr}$ is the critical necrosis threshold (0.1 μM) and $R_{max}$ is the maximal consumption rate. Two values for $R_{max}$ often cited in the literature of 16 μMs$^{-1}$ and 34 μMs$^{-1}$ were used to generate upper and lower bounds of the viability fraction (f) plots. We used the step function, $$\theta(c > c_{cr}) = \begin{cases} 1, & \text{if } (c > c_{cr}) \\ 0, & \text{if } (c < c_{cr}) \end{cases}$$

so that cells were alive when the $O_2$ concentration was above c, and consumed $O_2$ or they were dead when the $O_2$ concentration was below $c_{cr}$ and had consumed all of the available $O_2$.

Simulations indicated that the fraction of viable cells depends upon the microwell volume, face porosity, encapsulated cell density and cellular $O_2$ consumption rate. Cell viability was observed to be consistently higher in microwells with 3D porosity as compared to 2D porosity (FIGS. 8c-8e). The spatial variation of viable cells within 2D and 3D microwells indicated that cells are more viable adjacent to porous faces (FIGS. 8c and 8d). This improvement was more pronounced in microwells with larger volumes and lower pore density. A notable simulation result is that cell viability was significantly higher when microwells feature 3D porosity and differences in viability as high as a factor of four were observed.

Since viability also depends on the number of cells encapsulated within the microwell, we simulated varying cell densities or cellular $O_2$ consumption within 500 μm sized microwells (FIG. 8f). The cell density (ρ) variation inside the microwells was modeled by varying the bulk $O_2$ consumption rate according to $$R = \rho \times R_{max} \times \frac{c}{c + c_{mm}} \times \theta(c > c_{cr}).$$

In the model, we assumed that all cells consume $O_2$ at the same rate and they have a close packed, uniform spatial distribution within the microwell. Simulations revealed that for all cell densities greater than approximately 5%, a significantly higher fraction of viable cells was consistently observed in 3D microwells.

Guided by numerical simulations and by the well-known fact that in vivo cells further than approximately 200 μm from the nearest blood vessel become hypoxic (R. H. Thomlinson and L. H. Gray, Br. J. Cancer, 1955, 9, 539-549), we chose 500 μm microwells to conduct a model experimental study. It should be noted that depending on the application (e.g. cell encapsulation therapy), the microwell size could be determined by a balance between encapsulating the largest numbers of cells for an improved therapeutic effect (by using larger wells) while providing adequate diffusion so that cells remain viable (by increasing surface to volume ratio achieved by using smaller wells). Many cell encapsulation devices such as alginate microspheres have diameters ranging from 400 to 800 μm (P. Devos, B. DeHaan, J. Pater and R. VanSchilfgaarde, Transplantation, 1996, 62, 893-899).

Figures 9A, 9B, 9C, 9D, 9E, 9F, 9G:
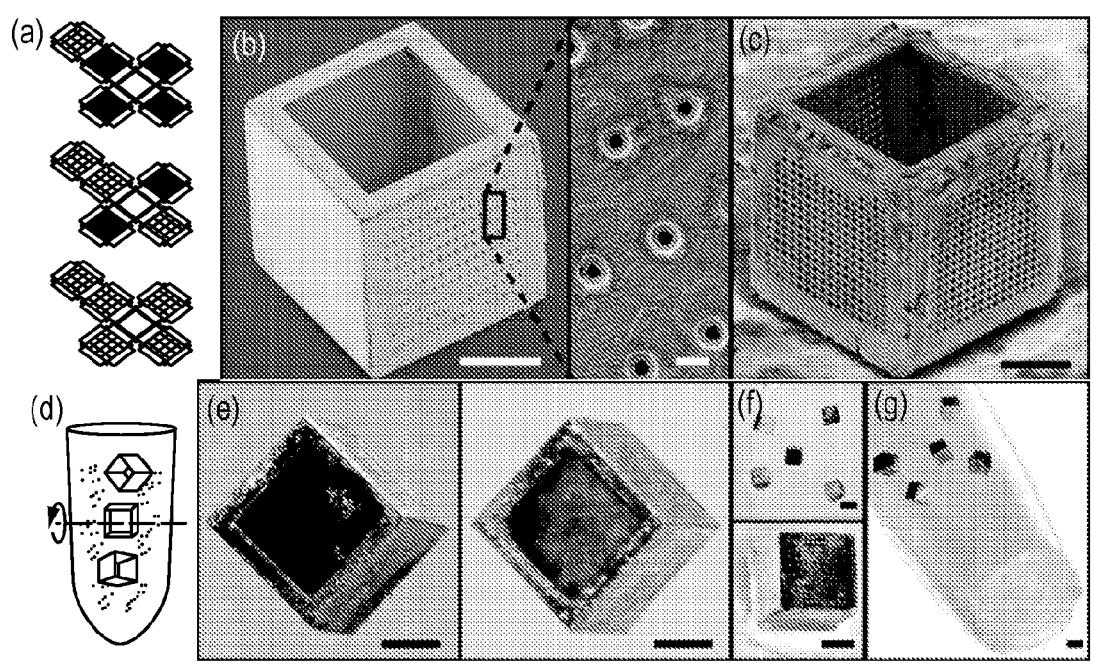
FIG. 9a is an example of layouts of the 2D templates for one, three and five porous-faced microwells according to an embodiment of the current invention. In each case, one panel had a large opening for cell loading.
FIG. 9b is an electron microscopy image of a 2D (one porous-faced, which self-assembled from the 2D template at the top panel of FIG. 9a) microwell along with a zoomed-in image showing individual pores according to an embodiment of the current invention.
FIG. 9c is an electron microscopy image of a 3D (five porous-faced, which self-assembled from the 2D template at the bottom of panel of FIG. 9a) microwell according to an embodiment of the current invention. The scale bar for the microwell images and inset indicates lengths of 200 µm and 10 mm respectively.
FIG. 9d is a conceptual schematic diagram of the cell-loading process which involves tumbling the microwells in a concentrated $10^4$ cells $ml^{-1}$ solution according to an embodiment of the current invention.
FIG. 9e show representative optical microscopy images of stained cells loaded via tumbling illustrating microwells with low (left) and high (right) cell number (scale bar 200 µm).
FIG. 9f is an optical microscopy image of five microwells arrayed and sealed on a polyurethane adhesive (scale bar 500 µm) with an inset showing the seal around the base of an individual microwell (scale bar 200 µm) according to an embodiment of the current invention.
FIG. 9g shows an optical microscopy image of a microwell array formed on a curved flexible substrate (scale bar 500 µm) according to an embodiment of the current invention.

Individual microwells were self-assembled (B. Gimi, T. G. Leong, Z. Gu, M. Yang, D. Artemov, Z. M. Bhujwalla and D. H. Gracias, Biomed. Microdevices, 2005, 7, 341-345) from 2D cruciform shaped templates composed of hollow, porous or closed square panels interconnected with solder hinges (FIG. 9a). Self-assembly was driven by the minimization of surface area of the molten hinges and has been described in detail elsewhere (T. G. Leong, P. Lester, T. Koh, E. Call and D. H. Gracias, Langmuir, 2007, 23, 8747-8751). A variety of polyhedral shapes with side lengths ranging from 100 nm to 2 mm, pore sizes as small as tens of nanometers, and with metallic or polymeric composition have been synthesized using this approach (T. G. Leong, A. Zarafshar and D. H. Gracias, Small, 2010, 6, 792-806; C. L. Randall, T. G. Leong, N. Bassik and D. H. Gracias, Adv. Drug Delivery Rev., 2007, 59, 1547-1561; C. L. Randall, A. Gillespie, S. Singh, T. G. Leong and D. H. Gracias, Anal. Bioanal. Chem., 2009, 393, 1217-1224; A. Azam, K. Laflin, M. Jamal, R. Fernandes and D. H. Gracias, Biomed. Microdevices, 2010, DOI: 10.1007/s10544-010-9470-x). The fabrication process is highly parallel and large numbers of polyhedra can be fabricated in a cost-effective manner. Here, a model geometry was designed in which we systematically varied the number of porous faces of 500 μm sized, cubic microwells between one (FIG. 9b), three and five (FIG. 9c); one face was left open for cell loading. Diffusion in the cubic microwells with one porous face mimics that of conventional 2D microwells, which typically have openings in only one plane; five porous-faced cubic microwells represent our example embodiment of 3D microwells. In all cases, pores were photolithographically structured as 10×16 arrays with individual sizes of 8 μm as-fabricated and 6 to 7 μm after gold (Au) coating. Au was electrodeposited onto all surfaces of the microwells to improve biocompatibility, since Au has been demonstrated to be inert to cells (B. Merchant, Biologicals, 1998, 26, 49-59) and can also be readily functionalized using a variety of thiol coatings to further enhance biocompatibility (J. C. Love, L. A. Estroff, J. K. Kriebel, R. G. Nuzzo and G. M. Whitesides, Chem. Rev., 2005, 105, 1103-1170).

As an alternative to the loading of conventional planar arrays using pipettes, microwells were loaded in a parallel manner via tumbling (FIG. 9d). Images of stained cells obtained within microwells indicated that there was variability in the number of loaded cells (FIG. 9e) within each microwell. However, since cells continued to multiply after loading, microwells had relatively homogeneous numbers of cells after incubation for 48 hours prior to first use. Haemocytometer counts that were obtained by counting trypsinized cells within microwells suggested cell numbers of $4.1\pm1.1$ ($\times10^4$) (average over a sample size, n=30) within each microwell after 48 hours.

Arrays were then formed by first orienting the microwells with their open face upwards using a glass pipette. The desired substrate, typically an adhesive tape or polyurethane adhesive spin-coated on a glass slide, was then brought into contact with the open face of multiple microwells to form the array. Sealing of the open microwell faces was complete when the polymer cured, typically within 30 minutes in cell media. Using this approach, arrays could easily be formed on both rigid (flat, FIG. 9f) and flexible (curved, FIG. 9g) geometries.

Figures 10A, 10B, 10C:
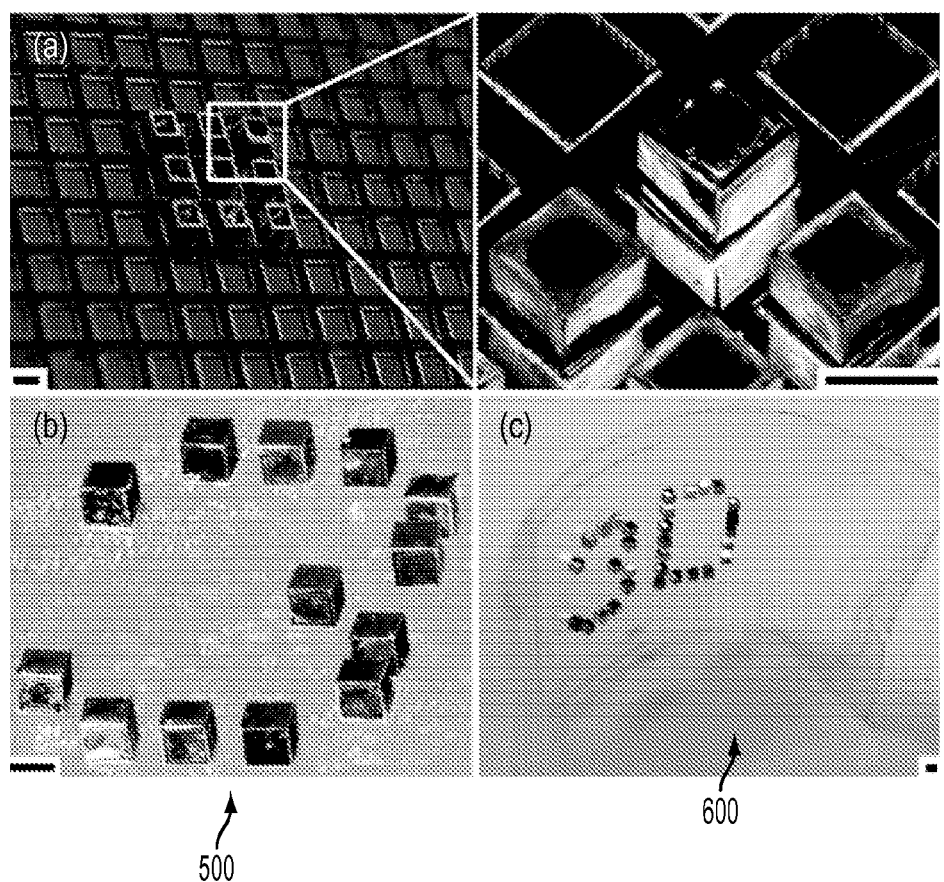
FIGS. 10a-10c show examples of arrays according to some embodiments of the current invention.

It was also possible to create array structures according to some embodiments of the current invention with both precisely positioned and spaced containers (microwells in this example) by first positioning the microwells in an SU-8 holder that was patterned with recessed slots (FIG. 10a). In addition to loading microwells with cells prior to positioning, they could also be loaded after positioning in the holder by allowing the cells to settle into the microwells. The desired array substrate was then brought into contact with the spatially positioned microwells thus creating arrays with relatively well defined geometric spacing. The ordered array structure "3D" including a flat substrate 500 (FIG. 10b) and including curved substrate 600 (FIG. 10c) according to some embodiments of the current invention highlights the utility of this approach.

The relative functionality of β-TC-6 cells encapsulated within 2D versus 3D microwell arrays was assessed by measuring insulin release, as would be typically required in a therapeutically relevant device, over time periods ranging from one day to approximately one month. The insulin concentration was measured using an insulin enzyme-linked immunosorbent assay (ELISA) and was recorded from arrays composed of one, three or five porous faces. We observed a significant difference between the insulin release characteristics from 3D microwell arrays as compared to 2D microwell arrays. For example, the initial insulin release rate in response to glucose stimulation was significantly more rapid from 3D microwell arrays (FIG. 11a).

Figures 11A, 11B, 11C, 11D:
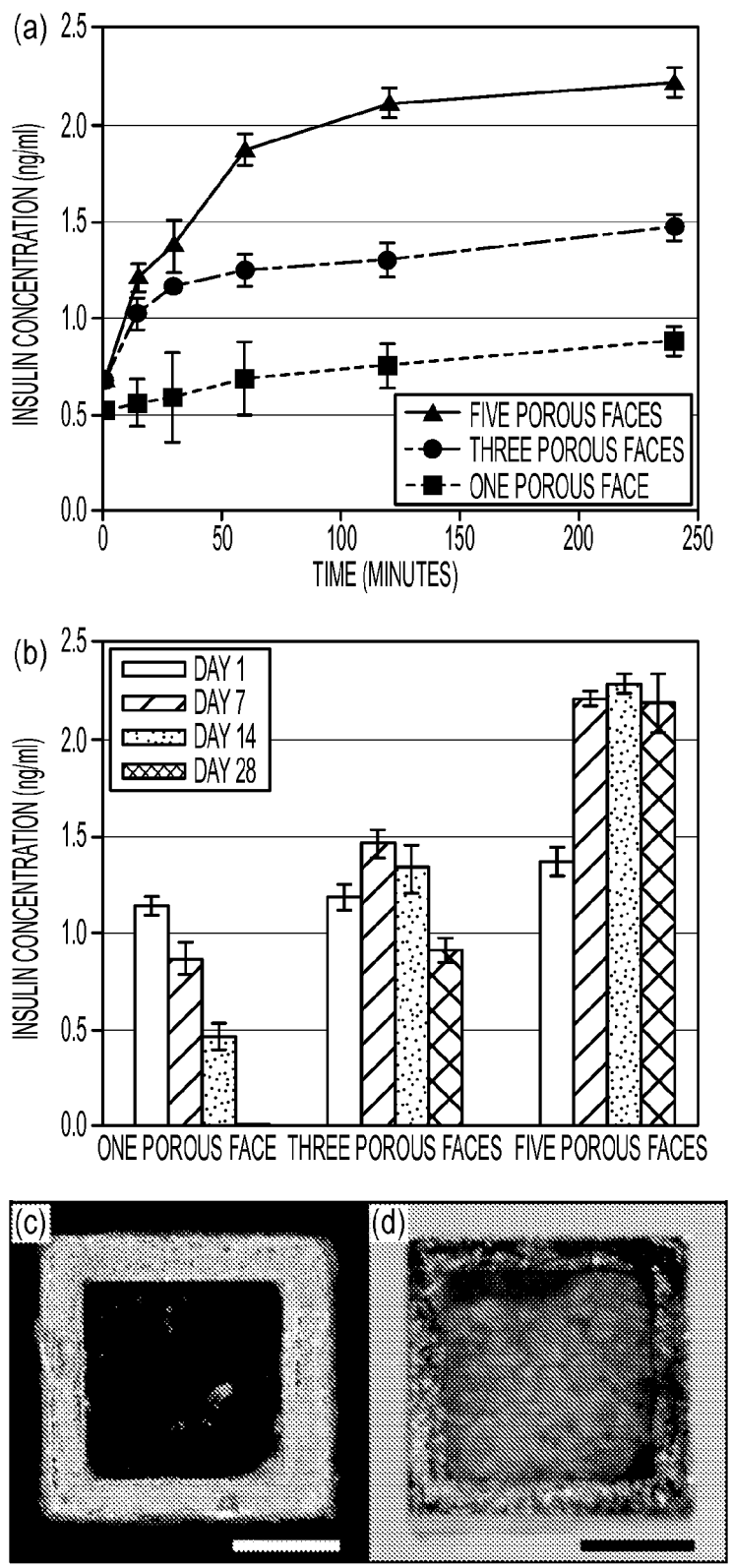
FIG. 11a shows insulin response profiles to a glucose stimulation from one, three and five porous-faced microwell arrays after seven days according to an embodiment of the current invention. Data are plotted as the average±the standard deviation (sample size n=5).
FIG. 11b is a graph showing the four hour (steady-state) insulin concentration measured in response to a glucose stimulation for b-TC-6 cells encapsulated within 2D (one porous-faced), three porous-faced and 3D (five porous-faced) microwell arrays. The average and the standard deviation obtained on days 1 (number of samples, n=5), 7 (n=5), 14 (n=3) and 28 (n=3) are plotted. The 3D microwell arrays produced significantly greater stimulated insulin at longer times. Representative fluorescence images of 2D FIG. 11c and 3D FIG. 11d 500 µm sized microwells removed from the array after 7 days. Cells were stained using the Live/Dead (green/red) assay. Microwells with one porous face showed significant numbers of dead cells while those with five porous faces showed high cell viability (scale bar 200 µm).

Additionally, over multiple trials, we found that while insulin release in response to the same glucose stimulation, at steady-state (240 minutes), from the one, three or five porous-faced microwell arrays was similar after encapsulation for one day, the 3D microwell arrays stimulated far greater insulin production after cells were encapsulated for longer durations (FIG. 11b). Specifically, after 28 days, the insulin released from five porous-faced microwell arrays was approximately $2.20\pm0.14$ ng ml$^{-1}$ as compared to $0.91\pm0.06$ ng ml$^{-1}$ for three porous-faced microwells. After 28 days, no measurable insulin was produced from 2D microwell arrays, while 3D microwell arrays maintained their insulin concentration levels.

In order to investigate the reason for the significantly enhanced insulin production by 3D microwell arrays as compared to 2D microwell arrays, we removed (peeled-off) individual microwells from the substrates at different time points and performed a Live/Dead cytotoxicity assay on the cells contained within. Starting from our 7 day measurement, we consistently observed significantly higher numbers of live cells within the 3D microwells as compared to the 2D microwells (FIGS. 11c and 11d). This result is in agreement with our simulations and provides an explanation for the insulin measurement results. We note that the numerical simulations presented in FIG. 8e are of microwells containing cells at higher cell densities in order to simulate the formation of a necrotic core. At similar cell densities that were used in the experiments (approx. 20%, corresponding to the dotted line in FIG. 8f and the corresponding image in FIG. 8d), minimal cell death was indeed predicted by simulations (<5%) as is consistent with the Live/Dead assayed 3D microwell arrays (FIG. 11d).

It should be noted that simulations only look at viability based on $O_2$ diffusion, but in reality cell viability is also dependent on other factors. For example, it is known that necrotic cells release chemicals that can impair the viability of proximal live cells, which could also contribute to the differences in observed cell viability over time between 2D and 3D porous-faced microwells. We hypothesize that this factor may also account for the continuously decreasing cell viability (and the corresponding decrease in insulin release) observed at long encapsulation times in 2D microwells (FIG. 11b).

In summary, both our simulations and experiments clearly indicate that 3D microwell arrays provide a significantly improved cell culture platform (in terms of enhanced diffusion and cell viability) as compared to widely utilized conventional 2D microwell arrays. In this example, we have focused on insulin secretion and cell viability based on nutrient diffusion. However, other aspects of individual cell behavior such as genetic expression or cellular morphology may also be altered when cells are cultured in more physiologically relevant 3D systems; these studies can be carried out using our 3D microwell arrays according to an embodiment of the current invention. As compared to other methods for culturing cells in geometries that enable 3D perfusion, our methodology affords high precision in terms of pore definition, size and spacing of cellular clusters. The 3D microwells enable cellular clusters to be precisely positioned on substrates in liquid culture media without the need for a gel matrix. If required, cells cultured in gel matrices can also be encapsulated. Additionally, fabrication of arrays that incorporate microwells with polymeric side walls would enable in situ viewing of encapsulated cells for in vitro cell culture applications. Our insulin release results indicate the therapeutic relevance of the 3D microwell array architecture for constructing bioartificial devices and for cell encapsulation therapy. For these in vivo applications, the ability to structure arrays of these microwells even on curved substrates could more accurately mimic anatomically relevant geometries.

The above examples describe some examples of array structures according to some embodiments of the current invention. However, the invention is not limited to those particular examples. A wide range of substrates or other supporting structures could be used as components of arrays according to some embodiments of the current invention. The substrates can be rigid in some embodiments. Rigid substrates such as glass, polystyrene dishes, silicon wafers, polycarbonate are suitable for some applications. However, other rigid substrates can be used without departing from the general concepts of the current invention. In other embodiments, the substrates can be flexible. For example, flexible substrates can be, but are not limited to, paper, a polymer, cloth, or combinations thereof.

Figures 12A, 12B, 12C:
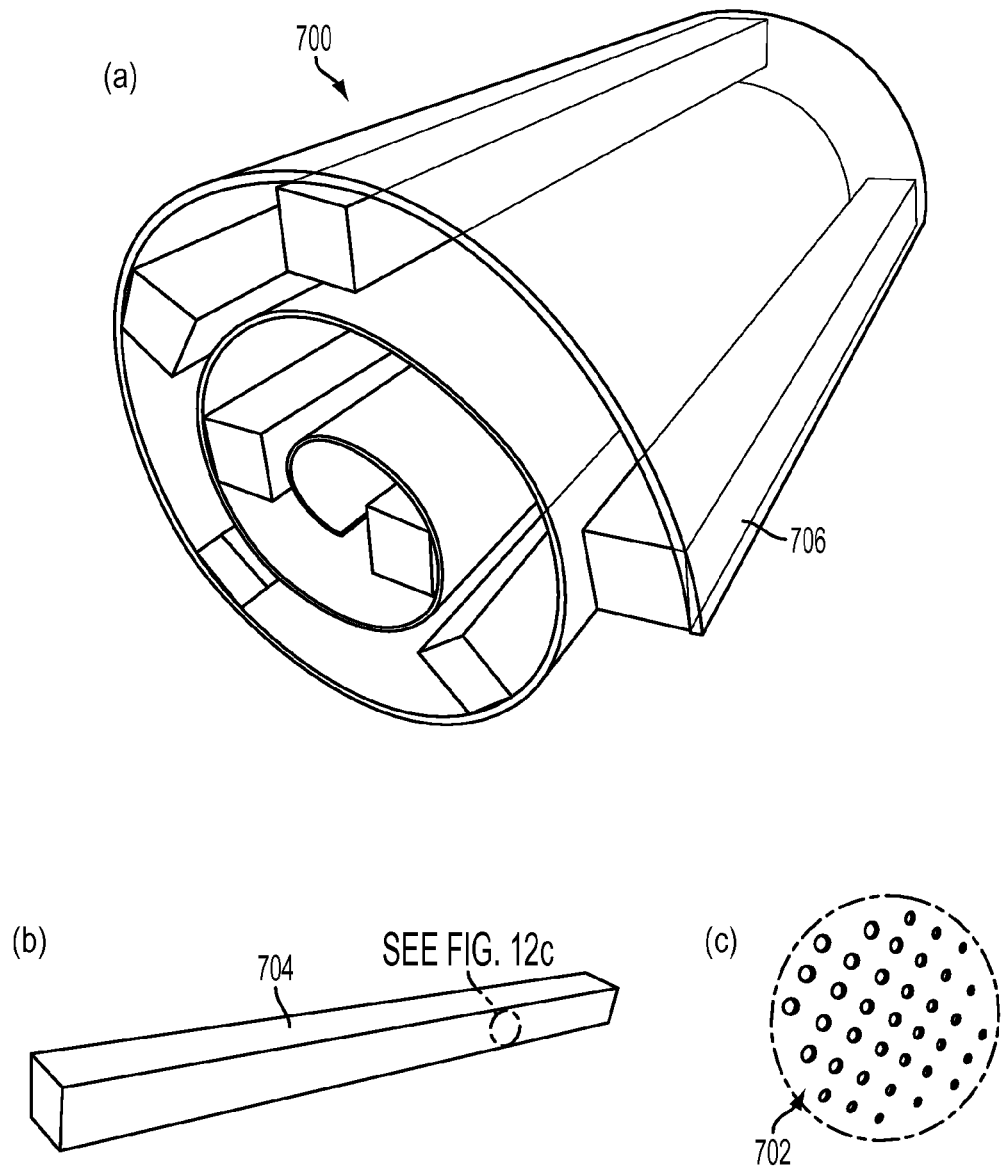
FIGS. 12a-12c provide a schematic illustration of a bio-artificial pancreas according to an embodiment of the current invention.

Another embodiment of the current invention is directed to a device for treating diabetes. The ultimate goal in treating a person with Type 1 diabetes is to mimic the natural insulin response of a non-diabetic person, so that patients do not even know they are suffering from the disease. An embodiment of the current invention is directed to a bio-artificial pancreas (BAP). The precise methods in micro and nanoscale engineering according to some embodiments of the current invention can overcome the limitations of existing pancreatic islet cell transplant devices. FIGS. 12a-12c provide a schematic illustration of a bio-artificial pancreas 700 according to an embodiment of the current invention. Techniques described above for forming containers and array structures can be used to provide immunoisolation and diffusion in a compact 3D form. FIG. 12a shows the overall centimeter-scale architecture of the BAP device 700 featuring rectangular parallelepiped containers such as 704 (FIG. 12b) having pores 702 (FIG. 12c), precisely arrayed 704 and sealed in a rolled alginate sheet 706. FIG. 12a illustrates seven containers. In this embodiment, each container is a gold coated container having a precise shape and size to ensure that no encapsulated cell is more than 250 µm from the external medium. This ensures adequate nutrition and waste removal to all encapsulated cells, thereby reducing hypoxia. The surface of each container has precisely defined nanopores 702 for size-selective immunoisolation. Smaller molecules such as insulin can easily diffuse through the nanopores, but the diffusion of larger molecules such as antibodies is impeded. Additionally, the gold coated surfaces of the containers can be modified with molecular monolayers that resist protein adsorption to reduce biofouling and further enhance immunoisolaton.

One of the key challenges in encapsulating the large number of islet cells required to replicate human pancreas function is to incorporate an architecture such that all cells in the implant have adequate access to nutrients and waste removal. Using mass-transport computer simulations as well as experiments, we have elucidated the conditions required in terms of (a) density of encapsulated cells in each container, (b) container and pore geometry, and (c) container spacing in a spiral roll architecture. We experimentally confirmed that cells encapsulated within appropriately designed containers were alive and able to release insulin over different time periods (FIGS. 11a and 11b). Here, containers that featured porosity in all three dimensions greatly limited hypoxia, and insulin release characteristics were far superior to those that had porosity in one or two dimensions. Based on our models and experiments we have verified that such an architecture provides a suitable geometry for encapsulation of a large number of cells, while also offering the possibility as a shunt implant. The precision in terms of exact container geometry and spacing will indeed minimize hypoxia. The developed numerical simulation models (FIG. 13a-13d) also have predictive value in that they allow us to run simulations on variations in designs before implementing them.

Figures 13A, 13B, 13C, 13D:
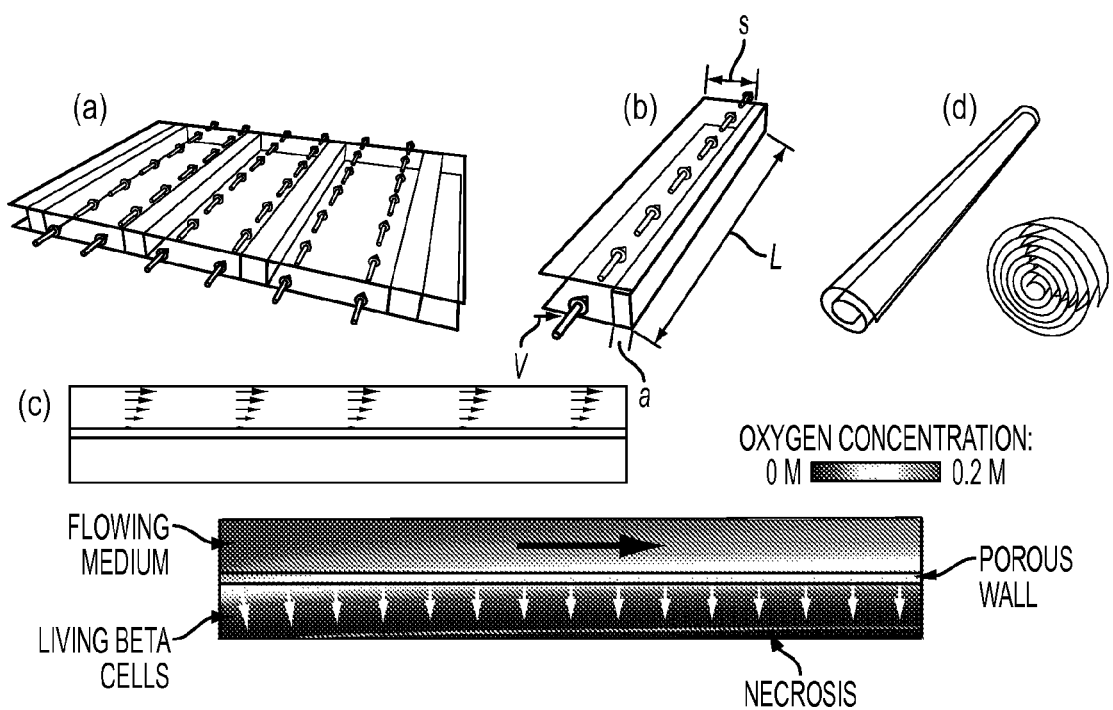
FIGS. 13a-13d show numerical simulations of medium flow and oxygen concentration that permit optimization of design parameters of a bio-artificial pancreas according to an embodiment of the current invention.

FIGS. 13a-13d show numerical simulations of medium flow and oxygen concentration that permit optimization of design parameters. In FIGS. 13a and 13b, a simplified view of the BAP 700 of FIG. 12a is more suitable for numerical analysis. In FIG. 13c, the velocity of medium flow and oxygen concentration near a single container that is filled with pancreatic beta cells is shown. Oxygen is depleted as medium flows past the container. In FIG. 13d, numerical simulations such as shown in part FIG. 13c will aid in the design of the BAP dimensions such as choosing between a "long and narrow" design of the BAP versus a "short and chubby" design.

Figures 14A, 14B, 14C, 14D, 14E, 14F, 14G:
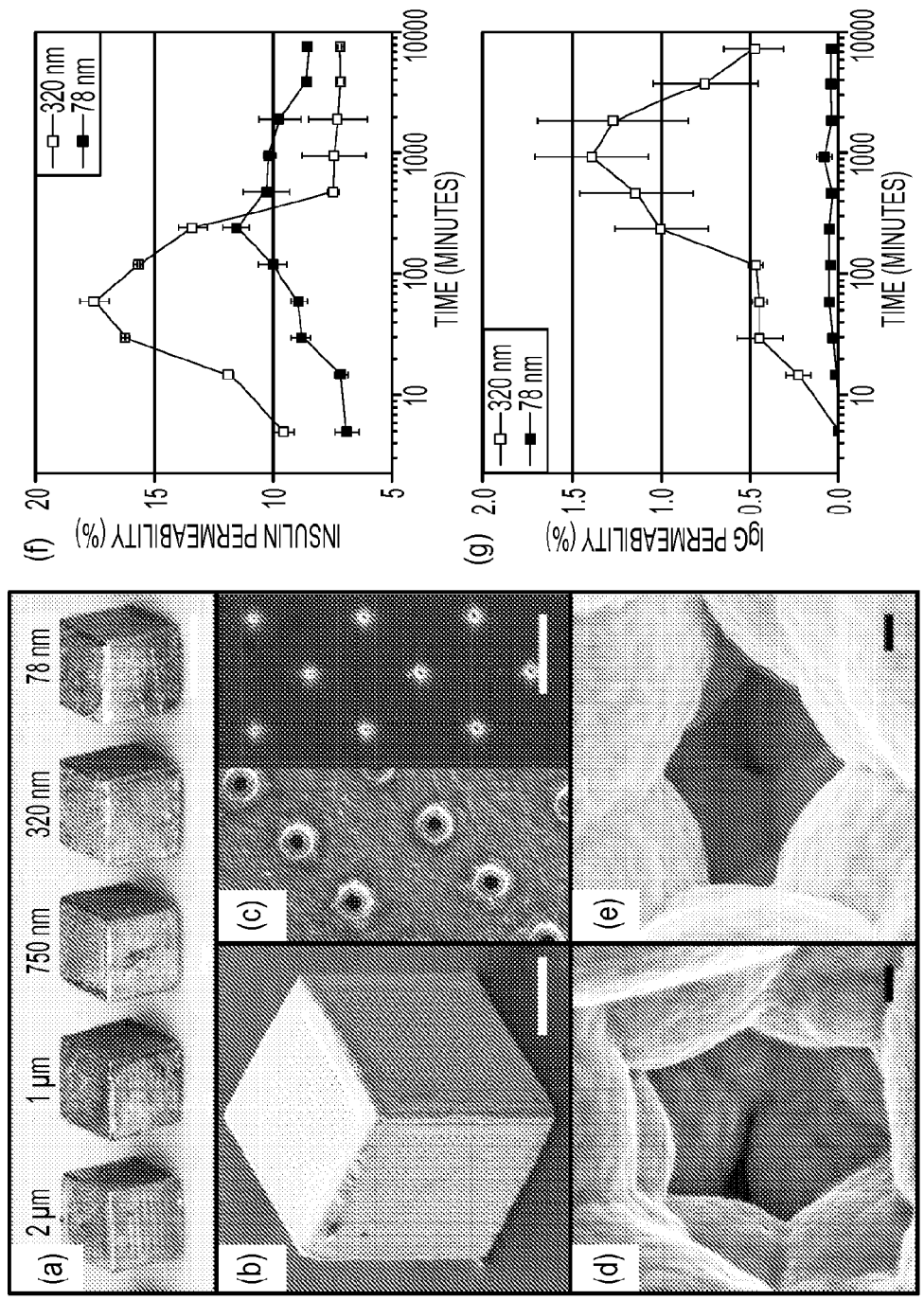
FIGS. 14a-14g provide data to show the effect of pore size of polyhedral containers in blocking large molecules while allowing small molecules to pass through according to an embodiment of the current invention.

As compared to polymeric or gel-based encapsulants, where it is difficult to precisely control the pore size and distribution, we have hypothesized that the precision of lithographic methods can be used to define pores with precise sizes, shapes, distributions and material composition. Hence, containers can be fabricated such that the side walls act as size-exclusion membranes that can significantly impede diffusion of immune components such as antibodies while not impeding the release of the smaller therapeutic molecule insulin. We investigated this hypothesis by fabricating cubic containers with systematically varying pore sizes of 2 µm to 78 nm (FIG. 14a). These containers were loaded with insulin and IgG and we confirmed that this approach of size-exclusion based immunoisolation does indeed work in that by choosing containers with appropriate pore sizes one can significantly impede diffusion of immune components (IgG; the smallest sized antibody) while permitting adequate diffusion of insulin.

FIG. 14a shows an optical image of cubic containers with precisely defined pore sizes ranging from 2 µm to 78 nm. According to some embodiments of the current invention, the porosity can be precisely defined in all three dimensions. FIGS. 14b-14e show progressively zoomed in images of a container with 78 nm pores. FIGS. 14f and 14g show permeability of insulin and IgG from containers with two different porosity shown over one week showing that the permeability of IgG slows as pore size decreases and was significantly impeded through 78 nm pores. Meanwhile, the movement of insulin out of containers with this pore size, was not significantly impeded. Data are presented as the average percent of initial concentration±the standard deviation (sample size, n=3).

Figures 15A, 15B, 15C:
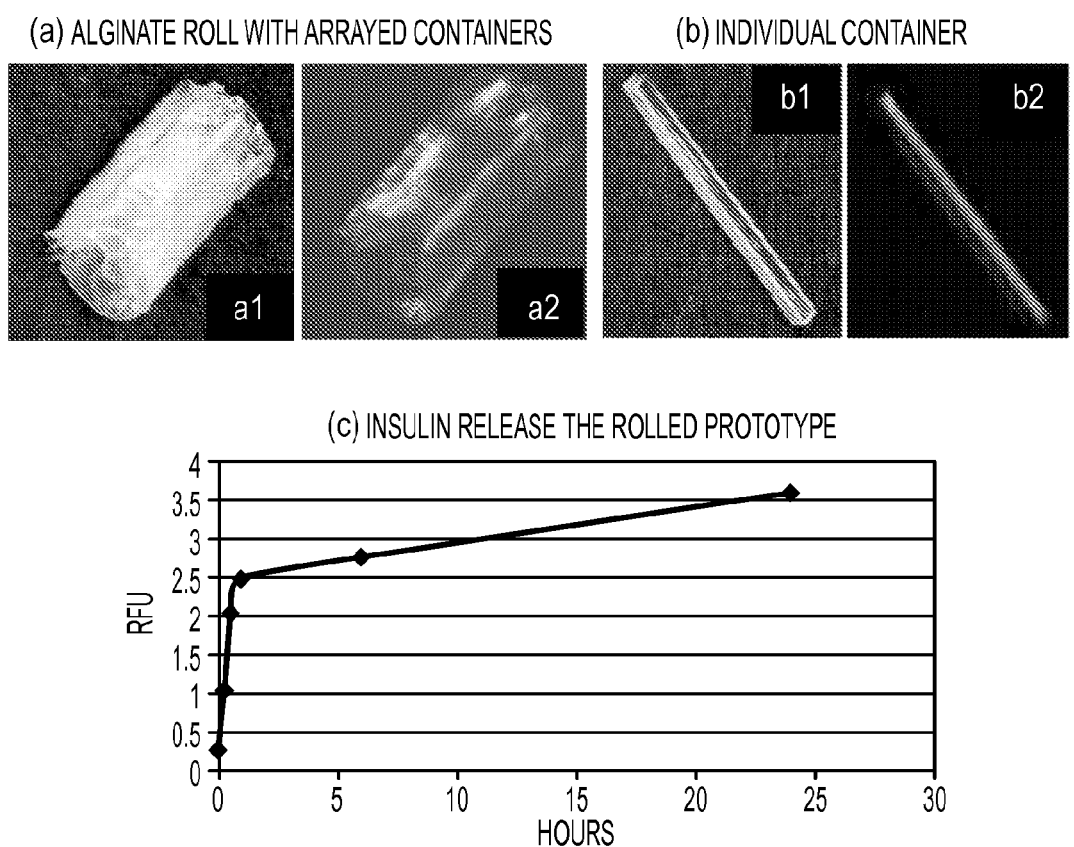
FIGS. 15a-15c show results for a working prototype of a BAP according to an embodiment of the current invention.

FIGS. 15a-15c show results for a working prototype of a BAP according to an embodiment of the current invention. As compared to cubic containers, parallelepiped shaped containers encapsulate much larger numbers of cells while retaining the 250 μm distance to the external environment along the length of the containers. Prototype devices have been fabricated with small numbers of containers to verify adequate sealing to alginate thin films in a roll. We verified insulin release from cells encapsulated within individual parallelepiped shaped containers as well as the rolled prototype. In FIGS. 15a and 15b, a1, b1 are bright field, and a2, b2 are fluorescence microscopy images of a prototype and individual container according to an embodiment of the current invention. The green color in the fluorescent image is from viable islet cells. In FIG. 15c, the insulin release from the prototype was also verified.

Another embodiment of the current invention is directed to programming moving chemical patterns in stationary media. According to this embodiment of the current invention, precisely patterned three-dimensional porous containers can be formed into an array structure to enable temporal control over chemical release. The containers can be fabricated by self-assembly from photolithographically structured two-dimensional panels as described above. Once fabricated, the containers can be filled with chemicals. The chemicals can be released by diffusion when the containers are submerged in a stationary medium. By varying the porosity, volume and shape of the containers it is possible to tune precisely when the chemicals are released. By arranging multiple containers with various temporal release characteristics in a gel it is possible to generate dynamic chemical patterns in a stationary medium. As an example application we show how multiple containers dispensed in a manner similar to inkjet printing can be used to generate "printable moving images". These can be used for artistic expression or in applications where precisely varying chemical patterns are required, for example.

It has been argued that in medicine the dose and time variation of the chemical concentration of a drug may be nearly as important as the chemical nature of the drug itself. Other applications, such as printing, may also benefit from precise control over the timing of chemical release as well. The precise temporal control over chemical release can readily be achieved when chemicals are released from containers whose geometry and wall porosity can be precisely patterned in all three dimensions according to some embodiments of the current invention. As compared to other methods (such as polymer microspheres) this technique can provide the advantage of allowing for precise control over the release via simple variations in container geometry. All the containers can be produced according to the same protocol, and no material variation is needed according to some embodiments.

Figures 16A, 16B, 16C, 16D:
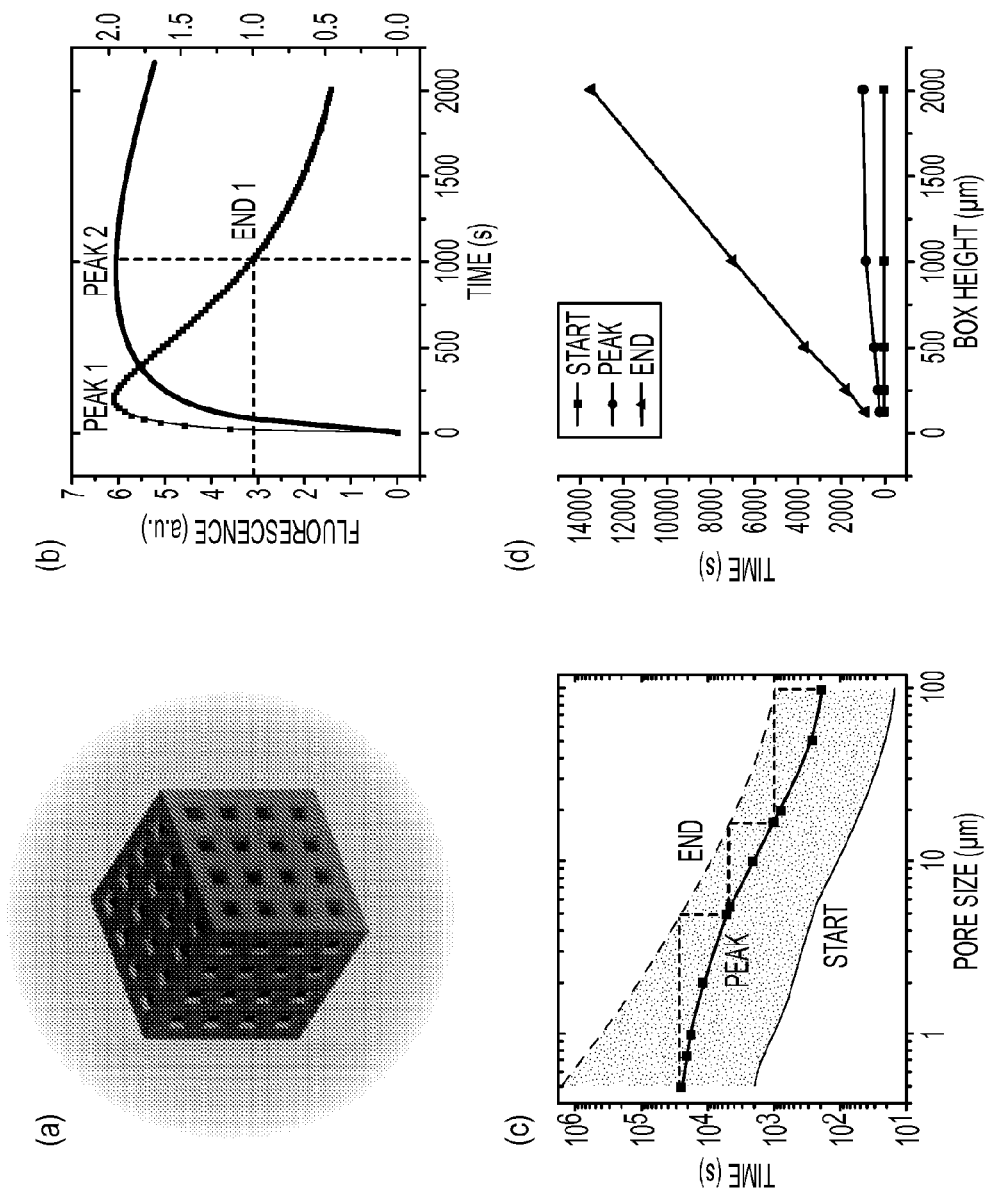
FIGS. 16a-16d illustrate some concepts of time-dependent chemical release and numerical estimates according to another embodiment of the current invention.

In this example, we will show that in addition to controlling the spatial shape of the chemical distribution, the container can be used to control timing of chemical release as well. To begin, let's consider one such parallelepiped-shaped hollow container with porous walls. When the container is filled with dye and submerged into a stationary medium the dye will start diffusing out of the container through the pores in the walls (FIG. 16a). Timing of the chemical release, such as its duration and to some extent the time when the chemical release "starts" can be adjusted by varying the container shape as well as by varying the porosity. Here, we define the "start" and "end" of the release as the time when the concentration in the vicinity of the container reaches a half (½) of its maximal value despite the fact that the decay occurs approximately exponentially and thus never fully reaches 0, Such definitions are necessary because for a continuous process such as passive diffusion with no external control it is impossible to create abrupt changes (mathematically described by step functions) in chemical concentration, which otherwise can be considered ideal. One typical temporal profile showing slow buildup and exponential decay is shown in FIG. 16b along with our definitions of the start and end of the release.

The duration of the chemical release in such a system is going to depend on the container volume and pore size: larger containers encapsulate more chemicals and given the pore size will release them for a longer time. Larger pores will result in quicker buildup of chemicals in the vicinity of the container and will shorten the duration of chemical release. Numerical simulations of chemical release from these containers confirm these predictions and further refine them. They show, for example, that the chemical concentration falls off much faster in the case of 5 pores as compared to just one. Results of numerical simulations of chemical release from cubic containers 500 μm in size with just one pore per face as a function of pore dimensions are shown in FIG. 16c. Variation in container size mainly affects the duration of chemical release while the pore size variation can be used to tune the moment the chemical release "begins". Thus it is possible via variation in container size and porosity to control and tune parameters of chemical release. In particular, it is possible to synchronize timing from different containers so that, for example, some containers will only start releasing chemicals by the time other containers have released almost all of their content. This opens up the possibility of "programming" various time-dependent chemical patterns by placing numerous properly designed containers in the immediate vicinity of each other. In particular, it is possible to "encode" time-dependent varying images into static structures; diffusion from these structures will then generate moving pictures in a stationary medium. The dashed line in FIG. 16c illustrates this process.

A conceptual outline of multiple containers with timings of release synchronized among all of them is presented in FIG. 17a-17f. Containers of various volumes with various pore sizes (FIG. 17a) are arranged in an array structure shown in FIG. 17c. In accordance with general ideas presented above, the containers' volume decreases along with the pore size. This is done to decrease the duration of release for containers that release chemicals later so that all "generations" of the image have approximately the same duration, i.e. we offset the effects of decreasing pore size and make duration of subsequent generation of chemical release closer to each other by decreasing the container volume. This process allows shortening the amount of chemical release time thus increasing the number of "generations" that can be produced within a given period of time (thus making it unnecessary to decrease pores beyond a certain limit).

Figures 17A, 17B, 17C, 17D, 17E, 17F:
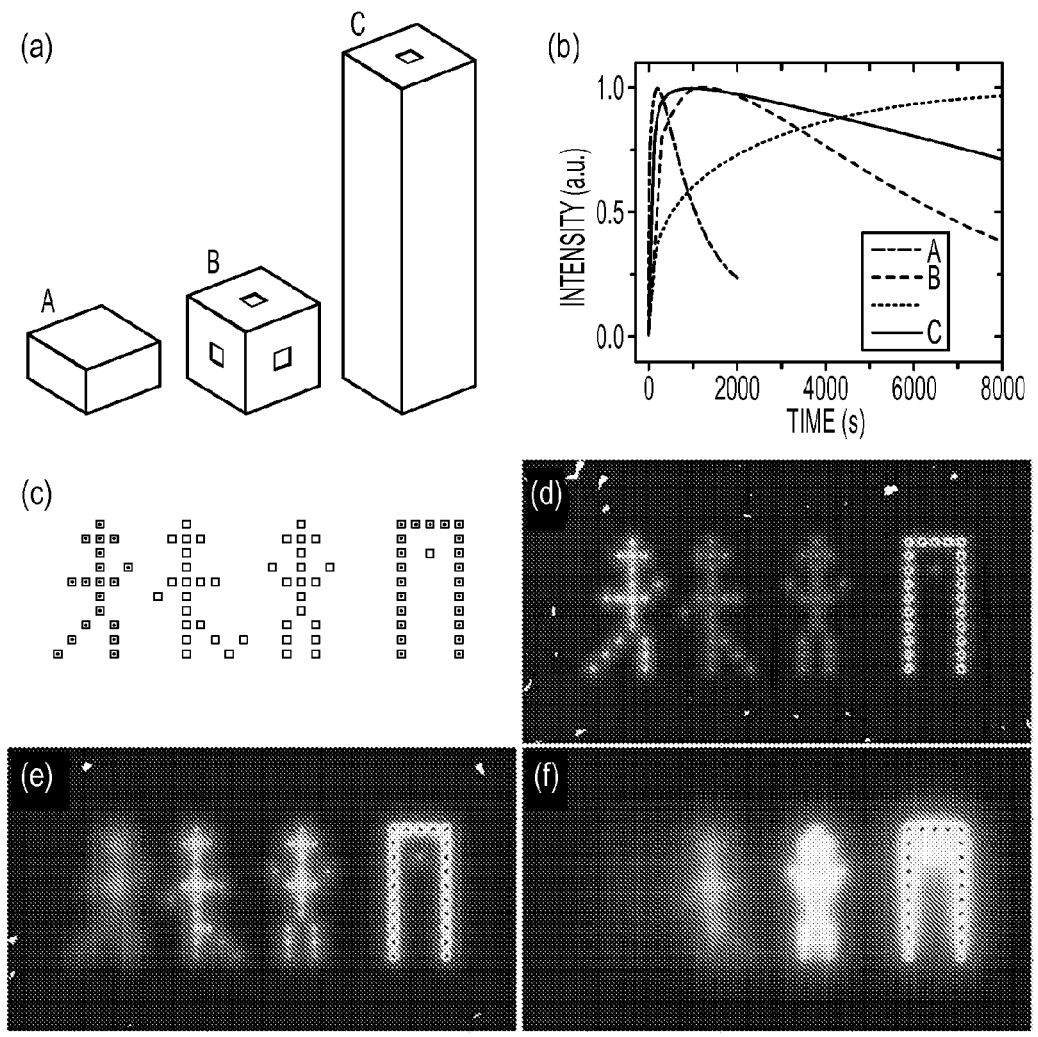
FIG. 17a-17f show an example of an animated patterns inside stationary media according to an embodiment of the current invention.
Figures 18A, 18B, 18C, 18D, 18E, 18F:
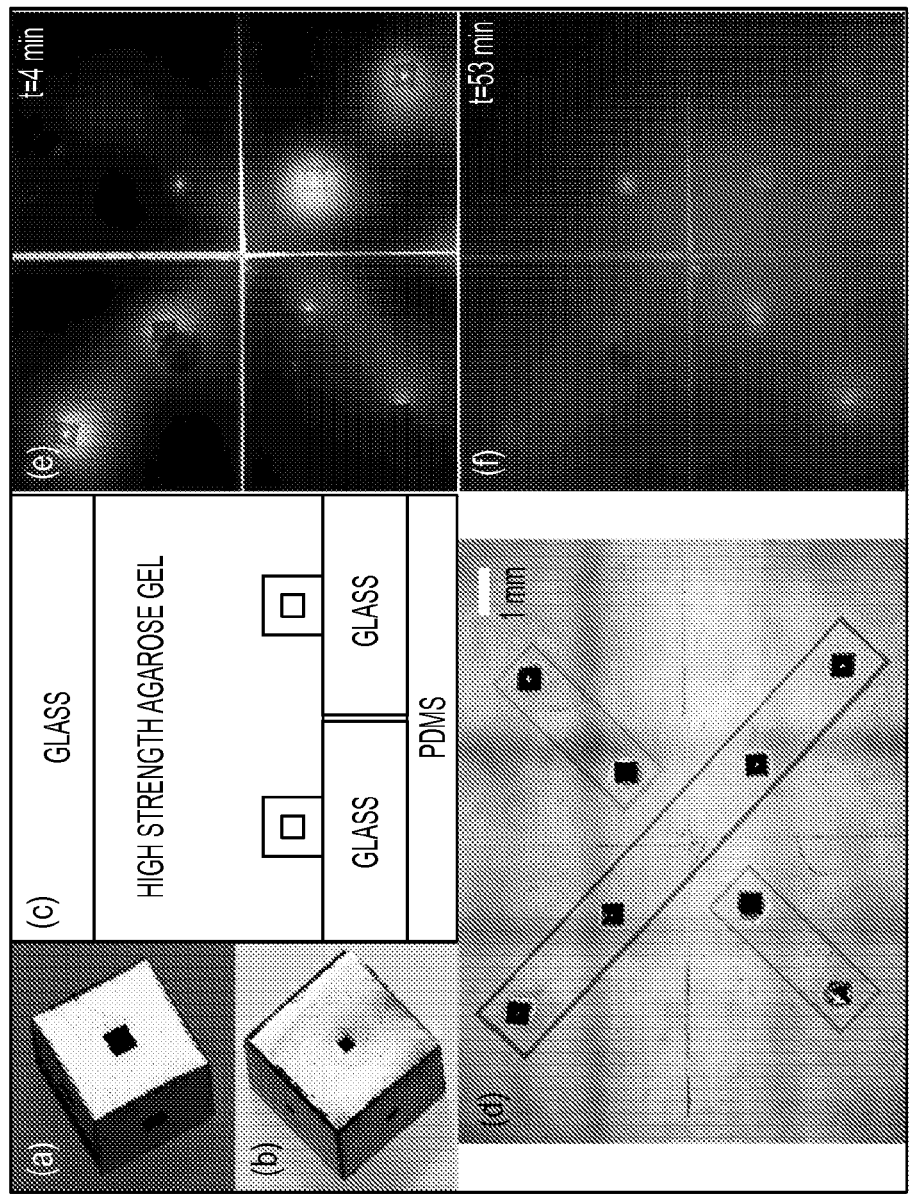
FIGS. 18a-18f show an experimental realization of moving chemical patterns in a stationary medium according to an embodiment of the current invention.
Figure 19A:
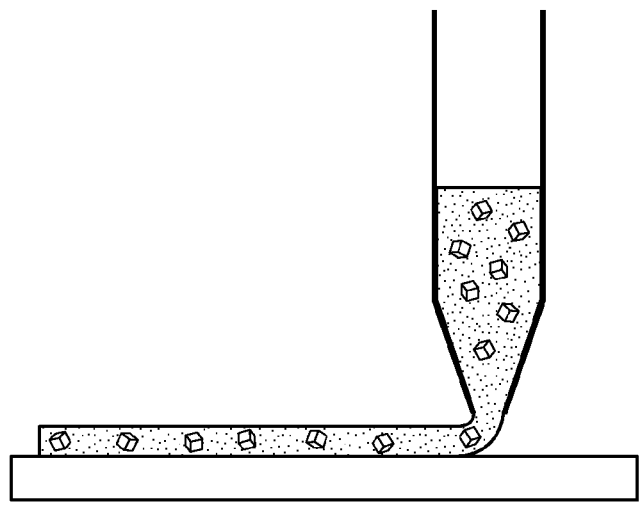
FIGS. 19a and 19b show fabrication methodology, color mixing and container rearrangement within the crate or on a substrate according to an embodiment of the current invention using "Inkjet"-like printing.
Figure 19B:
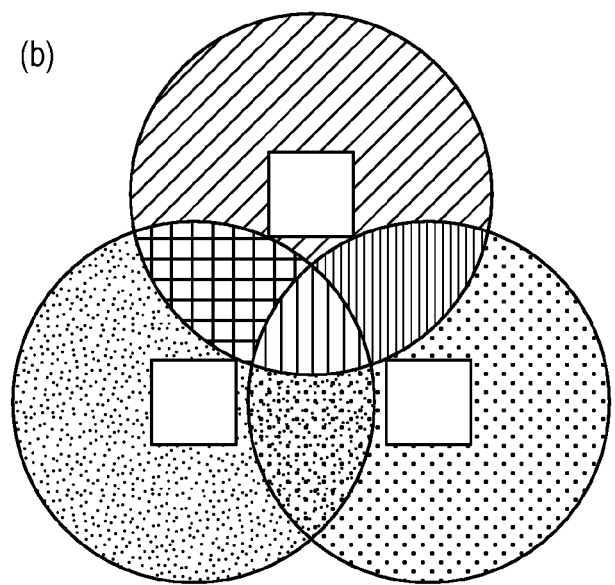

Graphs of chemical concentration in the vicinity of these containers are shown in FIG. 17b. The three generations of containers shown in FIG. 17a were arranged to produce the three shape of a running human figure. Containers comprising the ball and the gate were elongated to keep releasing chemicals for the whole duration of the animation. Once these containers are geometrically arranged in the sequence of shapes representing a moving human figure and filled with appropriate concentrations of the dye, they release this dye so that at first only the first human silhouette is visible as shown in FIG. 17d. As time goes by, the first "generation" of containers become empty while the second "generation" reaches its peak. The process is repeated for the third "generation".

It should be noted that the numerical simulations presented above assume a certain kind of boundary conditions. When working with multiple containers neighboring boxes will change the concentration in the vicinity of its neighbors which will have some effect on the chemical release from the box under consideration. While it is possible to optimize boxes for each surrounding, a more practical way is to just design a few fixed containers and then use them in different configurations.

Actual fabricated containers along with dynamic moving images of a fluorescent dye (uranine) diffusing out of the containers are shown in FIGS. 18a-18d. Here the containers were manually arranged on a grid as described previously to form an array structure. The containers can be filled with a variety of dyes and a broad gamut of colors can be generated by techniques similar to those employed in TV sets, i.e. containers with complementary dyes can be positioned close to each other and other colors can be generated by mixing. Arranging containers on a preexisting grid assures precise positioning and thus diffusion from containers can be calculated ahead of the actual experiment, and the container properties can be optimized for the planned layout. In this arrangement, this reconfigurable array of containers which release dye via diffusion resembles an actual display, such as a ubiquitous LCD screens, electrophoretic spheres (also known as eInk, reference) or a prototype microfluidic display (reference). The main difference between our display and other techniques is absence of external links in our case. Here the timing information is encoded in the "pixels" themselves. Absence of external links in our case allows the display to be handled separately from sources of information; additionally it has the potential to reduce the cost of such display production. The displays can be reused by refilling the containers with dyes. For example, in our case of containers bound to a rigid substrate it is possible to refill the containers by submerging the whole array into dye solutions with increasing concentrations for progressively shorter amounts of time.

According to this embodiment, the gel is printed along with the containers themselves to serve as a medium for the diffusion of the chemical. Containers can be fabricated in different colors either by plating metals such as gold on their exterior or by removing sacrificial metal layers (such as copper and chromium) from their exterior. This way, the color of the containers can be matched with the color of their background of the image allowing only the diffusing dye to be visible. This technique may provide a medium for a new form of artistic expression where painted images will have life of their own. In other embodiments, release of display images can also be by active control such as, but not limited to, electrically heating the containers. Additionally, the technique can be used in biotechnology to create varying chemical concentrations in cell culture.

Experimental Methods for Programming Moving Patterns

Numerical Simulations.

Numerical simulations were carried out using COMSOL Multiphysics (COMSOL, Inc.). Solutions of the time-dependent diffusion equation were sought in the geometry corresponding to the container with a pattern on it. The container was assumed to be surrounded by a stationary medium 4 mm thick. For most of the data shown in this embodiment we assumed zero boundary conditions thus disregarding the possibility that chemicals released by neighboring boxes affect chemical release from any given container.

Container Fabrication.

The patterns and slit shapes obtained in our numerical simulations were exported to AutoCAD (Autodesk, Inc.) and printed on masks at 40,000 dpi. The masks were used for fabrication of 2D panels and solder hinges following the procedures published previously (references). The panels with hinges were then released from the wafers and heated above melting point of solder at which point they spontaneously folded into 3D containers. The self-folding process was driven by a minimization of surface energy of the molten hinges and is described in detail elsewhere. The hinges were designed to completely seal the edges and the corners of the containers. Gold (Au) was coated on the inside and outside of the cubes by electrodeposition after assembly. The final size of the pores was determined by the duration and current density of electrodeposition.

Fabrication of the Container Arrays.

To form moving images the containers were spatially arranged to form desired figures and then glued to rigid substrates to form array structures according to an embodiment of the current invention. Two methods were used to create such arrays. In one, the containers were positioned in crates and a substrate with a thin film of spun glue was brought from the top. The containers then adhered to the film. Curing of the glue was done in an incubator that maintains temperature and humidity at elevated levels. Alternatively, a glass slide was positioned on top of the crates and the containers were individually attached using Gorilla glue to the slide. In this method the crates were not used to mechanically align the containers; instead, they served as "stencils" for subsequent visual alignment of containers. The slide was scratched with a dicer to both form a clean glass surface and to make the surface rougher which may improve glue adhesion. The glue was cured in the cell incubator.

Chemical Loading.

Once array fabrication was finished the containers were loaded with chemicals by soaking them in aqueous solutions overnight. In the case of small pores the containers were placed in a sealed chamber connected to a pump which allowed for changes in the atmospheric pressure. This was done to speed up loading and to assure absence of air bubbles inside the containers. The concentrations of chemicals to be loaded in the containers were calculated numerically in accordance with the graphs similar to the ones shown in FIG. 16 to make all containers appear similarly when the chemical release reaches its peak. We utilized solutions of uranine and other dyes in our experiments.

Imaging and Diffusion Studies.

Imaging of diffusion from fluorescein-filled containers was achieved by submerging the containers into either a 4 mm tall polydimethylsiloxane (PDMS) chamber that was filled with either with 4.5% (w/v) high strength agarose gel (to suppress convection and undesired flows). High viscosity gel was needed to minimize flow and disturbance to the containers while the gel was setting.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

As used herein, the term "two-dimensional," which can be abbreviated as "2D," refers to a figure, an object, or an area that has a height and a width, but no depth, and is therefore flat or planar. In contrast, the term "three-dimensional," which can be abbreviated as "3D," refers to a figure, an object, or an area that has a height, a width, and a depth.

As used herein, the terms "microscale" or "microstructure" refer to one or more structures that have at least one dimension, e.g., a height, width, length, and/or depth, in a range from about one micrometer (μm), i.e., 1×10$^{-6}$ meters, to about 999 μm, including any integer value, and fractional values thereof, including about 1, 2, 5, 10, 20, 30, 40, 50, 60, 70, 80, 90, 100, 200, 500, 600, 700, 800, 900, 999 μm and the like.

As used herein, the terms "patterned" and "micropatterned," and grammatical variants thereof, are used interchangeably and refer to any arbitrary two-dimensional pattern having microscale features, i.e., features having at least one dimension, e.g., a height, width, length, and/or depth, in a range from about one um to about 999 um, as those ranges are defined herein below. In some embodiments, the two-dimensional pattern can have a sub-micrometer dimension, i.e., a dimension having a range from about 0.1 μm to about 0.999 μm.

The terms "photolithography," "photo-lithography," or "photolithographic process" refer to a lithographic technique in which precise patterns are created on a substrate, such as a metal or a resin, through the use of photographically-produced masks. Typically, a substrate is coated with a photoresist film, which is dried or hardened, and then exposed through irradiation by light, such as ultraviolet light, shining through the photomask. The unprotected areas then are removed, usually through etching, which leaves the desired patterns.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth. The term "plurality" as used herein means "one or more."

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments±50%, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

The embodiments discussed in this specification are intended to explain concepts of the invention. However, the invention is not intended to be limited to the specific terminology selected and the particular examples described. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. An array structure comprising;
a substrate having a surface with a plurality of recessed slots; and
a plurality of containers arranged in a predetermined pattern with respect to each other in at least some of said recessed slots of said substrate, each of the plurality of containers having a spherical or polyhedral shape,
wherein each container of said plurality of containers is attached to the substrate or to another container of said plurality of containers,
wherein each container of said plurality of containers has an enclosing structure defining a plurality of pores and has a maximum outer dimension that is less than about 1 mm,
wherein each container of said plurality of containers has a substantially predetermined porosity, and
wherein at least one pore of said plurality of pores is facing a direction that is non-coplanar with a plane defined by directions of at least two other of said plurality of pores such that said substantially predetermined porosity is a three-dimensional porosity.

2. An array structure according to claim 1, wherein each container of said plurality of containers has a maximum outer dimension that is less than 1 mm and greater than 1 nm.

3. An array structure according to claim 1, wherein each side of each container of said plurality of containers defines at least one pore of a predetermined dimension to provide said predetermined porosity.

4. An array structure according to claim 3, wherein said at least one pore has an effective diameter of at least 0.5 nm and less than 1 mm.

5. An array structure according to claim 3, wherein said at least one pore has an effective diameter that is smaller than a first molecular species such that said first molecular species will be blocked from passing through said at least one pore, and wherein said at least one pore has an effective diameter that is larger than a second species of molecules such that said second species of molecules can pass through said at least one pore.

6. An array structure according to claim 1, wherein said plurality of containers are arranged along a two-dimensional surface of said substrate.

7. An array structure according to claim 1, wherein said plurality of containers are arranged to form a three-dimensional array.

8. An array structure according to claim 1, wherein said plurality of containers are arranged with a space of at least 1 nm between adjacent containers and less than 1 cm.

9. An array structure according to claim 1, further comprising at least one of a liquid chemical, a protein, a polymer, a bacteria, a mammalian cell, or combinations thereof contained within each of said plurality of containers.

10. An array structure according to claim 1, wherein said substrate is a rigid substrate.

11. An array structure according to claim 1, wherein said substrate is a flexible substrate.

12. An array structure according to claim 11, wherein said flexible substrate is at least one of a paper, polymer, or cloth substrate.

13. An array structure according to claim 1, wherein said plurality of containers comprise containers that have sizes and porosities selected such that a liquid contained in each container will diffuse substantially at a predetermined rate into a surrounding medium, said array structure providing a dynamic visual image while in operation.

14. An array structure according to claim 1, wherein said plurality of containers are self-folding containers.

15. An array structure according to claim 1, wherein said plurality of containers are polymer containers.

16. An array structure according to claim 1, wherein said plurality of containers are biodegradable containers.

17. An array structure according to claim 1, wherein said plurality of containers comprises containers of different sizes.

18. A bio-artificial pancreas, comprising:
a substrate having a surface with a plurality of recessed slots; and
a plurality of porous containers attached to said substrate in said recessed slots, each container of said plurality of porous containers having an enclosing structure defining a plurality of pores,
wherein each of the plurality of porous containers has a spherical or polyhedral shape and a maximum outer dimension that is less than about 1 mm,
wherein said plurality of porous containers are constructed to have a size, shape and porosity such that said plurality of porous containers are suitable to contain pancreatic islet cells therein, allow insulin produced by said pancreatic islet cells to pass therethrough, and provide immuno-isolation for said pancreatic islet cells, and
wherein at least one pore of said plurality of pores is facing a direction that is non-coplanar with a plane defined by directions of at least two other of said plurality of pores such that said substantially predetermined porosity is a three-dimensional porosity.

19. A bio-artificial pancreas according to claim 18, wherein the plurality of porous containers have pores that have an effective diameter between 0.5 nm and 1 μm.

20. A bio-artificial pancreas according to claim 18, where the substrate and the plurality of porous containers are configured to be implantable in a body of a patient.

21. A dynamic display device, comprising:
a substrate having a surface with a plurality of recessed slots; and
a plurality of containers attached to said substrate in a predetermined pattern in said recessed slots, each container of said plurality of containers having an enclosing structure defining a plurality of pores,
wherein each of the plurality of porous containers has a spherical or polyhedral shape and a maximum outer dimension that is less than about 1 mm,
wherein each container has a size, shape and porosity to allow a liquid to diffuse therefrom with a predetermined diffusion pattern as a function of time when said plurality of containers are immersed in a diffusion medium while in use, and
wherein at least one pore of said plurality of pores is facing a direction that is non-coplanar with a plane defined by directions of at least two other of said plurality of pores such that said substantially predetermined porosity is a three-dimensional porosity.

* * * * *